US010538750B2

(12) United States Patent
Yung et al.

(10) Patent No.: US 10,538,750 B2
(45) Date of Patent: Jan. 21, 2020

(54) METHODS AND COMPOSITIONS FOR BLOCKING OFF-TARGET NUCLEIC ACIDS FROM CLEAVAGE BY CRISPR PROTEINS

(71) Applicant: Agilent Technologies, Inc., Santa Clara, CA (US)

(72) Inventors: Chong Wing Yung, San Jose, CA (US); Andrew Kennedy, Sunnyvale, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 142 days.

(21) Appl. No.: 15/442,437

(22) Filed: Feb. 24, 2017

(65) Prior Publication Data
US 2017/0247671 A1 Aug. 31, 2017

Related U.S. Application Data

(60) Provisional application No. 62/301,369, filed on Feb. 29, 2016.

(51) Int. Cl.
*C12N 9/22* (2006.01)
(52) U.S. Cl.
CPC .............. *C12N 9/22* (2013.01); *C12Y 301/00* (2013.01)
(58) Field of Classification Search
None
See application file for complete search history.

(56) References Cited

U.S. PATENT DOCUMENTS

| 9,932,566 B2 * | 4/2018 | Kennedy .............. C12N 15/902 |
| 2014/0179006 A1 | 6/2014 | Zhang |
| 2014/0273226 A1 | 9/2014 | Wu |
| 2014/0273233 A1 | 9/2014 | Chen et al. |
| 2014/0295556 A1 | 10/2014 | Joung et al. |

FOREIGN PATENT DOCUMENTS

| WO | 2013176772 A1 | 11/2013 |
| WO | 2014099750 A3 | 10/2014 |
| WO | 2014144592 A3 | 12/2014 |
| WO | 2014144761 A3 | 10/2015 |
| WO | WO 2016022866 A1 | 2/2016 |

OTHER PUBLICATIONS

International Search Report and Written Opinion for PCT/US2017/019523 dated Feb. 24, 2017.
Kuscu, Cet, et al., "Genome-wide Analysis Reveals Characteristics of Off-target Sites Bound by the Cas9 Endonuclease", Nature Biotechnology, 2014, vol. 32, No. 7, pp. 677-683.
Kim, Daesik, et al., "Digenome-seq: genome-wide profiling of CRISPR-Cas9 off-target effects in human cells", Nature Methods, 2015, vol. 12, No. 3, pp. 237-243.
Cho, Seung Woo, et al., "Analysis of off-target effects of CRISPR/Cas-derived RNS-guided endonucleases and nickases", Genome Research 2014, vol. 24, 132-141.
Barker et al., "Increased DNA Microarray Hybridization Specificity Using sscDNA Targets", BMC Genomics. Apr. 22, 2005;6:57.
Carroll, D., "Staying on Target with CRISPR-Cas", Sep. 2013, Nature Biotechnology, vol. 31, 807-809.
Cho et al., "Target Genome Engineering in Human Cells with the Cas9 RNA-Guided Endonuclease", Nature Biotechnology, Jan. 29, 2013, vol. 31, 230-232.
Cong et al., "Multiplex Genome Engineering Using CRISPR/Cas Systems", Jan. 3, 2013, Science, Vol. 339, 819-823.
Fu et al., "Improving CRISPR-Cas Nuclease Specificity Using Truncated Guide RNAs", Nature Biotechnology, Jan. 26, 2014, vol. 32, No. 3.
Gasiunas et al., Cas9-crRNA Ribonucleoprotein Complex Mediates Specific DNA Cleavage for Adaptive Immunity in Bacteria, Proc Natl Acad Sci U S A., Sep. 4, 2012, 109(39): E2579-E2586.
Hou et al., "Efficient Genome Engineering in Human Pluripotent Stem Cells Using Cas9 from Neisseria meningitidis", Proc Natl Acad Sci U S A., Sep. 24, 2013;110(39):15644-15649.
Jinek et al., "A Programmable Dual-RNA-Guided DNA Endonuclease in Adaptive Bacterial Immunity", Aug. 17, 2012, Science, vol. 337 (6096): 816-821.
Kleinstiver et al., "Engineered CRISPR-Cas9 Nucleases with Altered PAM Specificities", Nature 523,481-485, (2015).
Mali et al, RNA-Guided Human Genome Engineering via Cas9, Feb. 15, 2013, Science, 339 (6121): 823-826.
Mojica et al., "Short Motif Sequences Determine the Targets of the Prokaryotic CRISPR Defence System", Microbiology, Mar. 2009; 155(Pt 3):733-40.
Ran et al., "Double Nicking by RNA-Guided CRISPR Cas9 for Enhanced Genome Editing Specificity." Cell 154(6), 1380-1389, Sep. 12, 2013.
Ran et al., "In Vivo Genome Editing Using *Staphylococcus aureus* Cas9", Nature 520(7546),186-191, Apr. 9, 2015.
Smith et al., "Whole-Genome Sequencing Analysis Reveals High Specificity or CRISPR/Cas9 and TALEN-Based Genome Editing in Human iPSCs", Cell Stem Cell, 15(1), 12-13, Jul. 3, 2014.
Tsai et al., "GUIDE-seq enables genome-wide profiling of off-target cleavage by CRISPR-Cas nucleases", Nature Biotechnology, Dec. 16, 2014.
Tsai et al., "Dimeric CRISPR RNA-guided FokI nucleases for highly specific genome editing", Nat. Biotechnol., June 214, 32(6), 569-576.

(Continued)

*Primary Examiner* — Channing S Mahatan

(57) ABSTRACT

This invention relates to reagents and methods for increasing specificity and efficiency of genome editing by CRISPR associated (Cas) protein systems, more particularly by Cas: guide RNA complexes, by blocking off-target nucleic acids from cleavage by Cas:guide RNA complexes.

20 Claims, 6 Drawing Sheets
Specification includes a Sequence Listing.

(56) References Cited

OTHER PUBLICATIONS

Veres et al., "Low Incidence of Off-Target Mutations in Individual CRISPR-Cas9 and TALEN Targeted Human Stem Cell Clones Detected by Whole-Genome Sequencing", Cell Stem Cell, 15(1), 27-30 Jul. 3, 2014.
www.addgene.org/CRISPR/, "CRISPR/Cas Plasmids and Resources", addgene: the nonprofit plasmid repository, Aug. 6, 2015.

* cited by examiner

SEQUENCE LISTING

```
<160> NUMBER OF SEQ ID NOS: 9

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205
```

```
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
            275                 280                 285
Leu Phe Leu Ala Ala Lys Asn Leu Ser Asp Ala Ile Leu Leu Ser Asp
290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
610                 615                 620
```

-continued

```
Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
```

Asn Gly Glu Ile Arg Lys Arg Pro Leu Ile Glu Thr Asn Gly Glu
            1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
            1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, t or u
<300> PUBLICATION INFORMATION:
<301> AUTHORS: Chen B, Gilbert LA, Cimini BA, Schnitzbauer J, Zhang W, Li GW, Park J, Blackburn EH, Weissman JS, Qi LS, Huang B
<302> TITLE: Dynamic imaging of genomic loci in living human cells by an optimized CRISPR/Cas system
<303> JOURNAL: Cell
<304> VOLUME: 155
<305> ISSUE: 7
<306> PAGES: 1479-91
<307> DATE: 2013-12-19

<400> SEQUENCE: 2
nnnnnnnnnn nnnnnnnnnn guuuaagagc uaugcuggaa acagcauagc aaguuuaaau    60
aaggcuaguc cguuaucaac uugaaaaagu ggcaccgagu cggugcuuuu uuu           113

<210> SEQ ID NO 3
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ggaaccauuc aaaacagcau agcaaguuaa aauaaggcua guccguuauc aacuugaaaa    60
aguggcaccg agucggugc                                                 79

<210> SEQ ID NO 4
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uagcaaguua aaauaaggcu aguccguuau caacuugaaa aaguggcacc gagucggugc    60

<210> SEQ ID NO 5
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
agcauagcaa guuaaaauaa ggcuaguccg uuaucaacuu gaaaaagugg caccgagucg    60
gugc                                                                 64

<210> SEQ ID NO 6
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
caaaacagca uagcaaguua aaauaaggcu aguccguuau caacuugaaa aaguggcacc    60
gagucggugc                                                           70

<210> SEQ ID NO 7
<211> LENGTH: 45
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 7
uagcaaguua aaauaaggcu aguccguuau caacuugaaa aagug                        45

<210> SEQ ID NO 8
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uagcaaguua aaauaaggcu aguccguuau ca                                      32

<210> SEQ ID NO 9
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uagcaaguua aaauaaggcu aguccg                                             26
```

METHODS AND COMPOSITIONS FOR BLOCKING OFF-TARGET NUCLEIC ACIDS FROM CLEAVAGE BY CRISPR PROTEINS

CROSS-REFERENCE TO RELATED APPLICATIONS

This application claims benefit of the filing date of and right of priority to U.S. Provisional Application No. 62/301,369, filed Feb. 29, 2016, which is incorporated by reference herein.

FIELD OF THE INVENTION

This invention relates to reagents and methods for increasing specificity and efficiency of genome editing by CRISPR associated (Cas) protein systems, more particularly by Cas:guide RNA complexes, by blocking off-target nucleic acids from cleavage by Cas:guide RNA complexes.

BACKGROUND OF THE INVENTION

Genome editing is a powerful technology for genetic manipulation and modification. A recently developed genome modification technology utilizes the bacterial clusters of regularly interspaced short palindromic repeats (CRISPR) associated protein 9 (Cas9), an RNA-guided DNA endonuclease, to induce a specific double-stranded break (DSB) at DNA target sites comprising a 3-nucleotide (nt) protospacer adjacent motif (PAM) and a 20-bp sequence complementary to the 5' end of a CRISPR guide RNA (gRNA) bound by Cas9. The guide RNA-Cas9 complex identifies and base pairs with its cognate DNA target sequence, resulting in target cleavage to form a DSB (FIG. 1). It has been observed that the CRISPR-Cas9 system tolerates a limited extent of base-pair mismatching between the DNA substrate and the 20-nt guide sequence of the guide RNA, which results in undesired off-target DNA cleavages (Carroll, D. (2013) *Nat. Biotechnol.*, 31, 807-9).

However, Cas9 cleavage of off-target nucleic acid sequences leads to unintended mutations, and that is a particular concern, such as for applications seeking to create clonal cell lines or germ lines without selection. Some studies have shown through whole genome sequencing (WGS) that there are very few unintended Cas9 mediated cleavage events. See Veres et al., "Low incidence of off-target mutations in individual CRISPR-Cas9 and TALEN targeted human stem cell clones detected by whole-genome sequencing." *Cell Stem Cell*, 15(1), 27-30 (2014); Smith et al., "Whole-genome sequencing analysis reveals high specificity or CRISPR/Cas9 and TALEN-based genome editing in human iPSCs." *Cell Stem Cell*, 15(1), 12-13 (2014). However, others contend that the low coverage of these WGS studies is insufficient to detect low-frequency events and that off-target cleavage events actually happen in higher frequency. Tsai et al., "GUIDE-seq enables genome-wide profiling of off-target cleavage by CRISPR-Cas nucleases." *Nature Biotechnology*; (December 2014).

As formation of off-target mutations is of profound concern to developers and users of genome editing technologies, three different strategies have been devised to improve the specificity of CRISPR-Cas9 genome modification (FIGS. 2A-2C). These strategies all reduce, but do not abolish, off-target DNA cleavage, and they do so at a cost of diminishing the on-target cleavage activity with respect to comparable unmodified CRISPR:Cas9 guided nuclease systems.

The first strategy involves a Cas9 mutant (Cas9n; also known as Cas9-D10A) that cleaves (or nicks) just one strand of the double-stranded DNA containing a target sequence. Two distinct guide RNA sequences are designed such that Cas9n creates offset nicks on opposite strands, thereby creating a DSB in the DNA target region (FIG. 2A). A variation of this strategy uses two different Cas9 mutants, each recognizing one of the two strands. Compared to an unmodified CRISPR-Cas9 system, this double nickase strategy requires two adjacent targetable DNA sequences and has lower on-target modification activity (Ran et al. (2013) *Cell*, 154, 1380-9). Additionally, although specificity is increased, there is still significant off-target activity, and single-stranded DNA nicks are weakly mutagenic (Mali et al., (2013) *Science*, 339, 823-6).

A second strategy employs cleavage-deactivated Cas9 (dCas9) fused to a dimeric-dependent FokI nuclease domain (FokI-dCas9) with two distinct guide RNAs specifying the DNA target site (FIG. 2B). Although this strategy has demonstrated greater specificity than that of the paired nickase strategy, it showed further reduction in on-target cleavage efficiency as compared to an unmodified CRISPR-Cas9 nuclease system using one or the other guide RNA of each pair (Tsai et al., (2014) *Nat. Biotechnol.*, 32, 569-76). Additionally, as with the paired nickase strategy, the FokI-dependent approach is limited by its requirement for two adjacent targetable DNA sequences, potentially restricting its utility and versatility in genome modification applications.

In a third strategy, improvement in the specificity of CRISPR-Cas9 cleavage was achieved by truncating the 20-nt guide sequence by 2 or 3 nucleotides at its 5' end to generate truncated guide RNAs (tru-RGNs, Fu et al., (2014) *Nat. Biotechnol.*, 32, 279-84). Comparing the DNA cleavage activity of full-length guide RNA and tru-RGNs targeting a few different genomic sequences, it was demonstrated that off-target cleavage activity can be reduced with tru-RGNs. However, for some DNA target sequences, off-target activities of tru-RGNs were still significant and even elevated in one instance relative to off-target activities of Cas9 complexed with full-length guide RNA. Additional truncation of the 5' end generally reduces on-target guide RNA-Cas9 activity, reducing it to background levels when the DNA-pairing sequence is truncated to 15 nt or shorter.

Researchers have sought to increase the specificity of CRISPR-Cas9 cleavage through use of truncated gRNA sequences (Fu et al., "Improving CRISPR-Cas nuclease specificity using truncated guide RNAs." *Nature Biotechnology*. (November 2013)) or paired-nickases (Ran et al., "Double nicking by RNA-guided CRISPR Cas9 for enhanced genome editing specificity." *Cell* 154(6), 1380-9 (2013). There is still a need for reagents and methods for increasing specificity and efficiency of RNA-guided genome editing.

BRIEF DESCRIPTION OF THE DRAWINGS

In FIG. 2A, the paired nickase strategy uses two copies of a Cas9 mutant (Cas9-D10A) to make offset single-stranded nicks at two DNA target sites directed by two distinct guide RNA sequences. In FIG. 2B, the dimeric RNA-guided FokI nuclease strategy fuses a catalytically inactive Cas9 protein (dCas9) to a dimerization-dependent FokI nuclease domain.

Two guide RNAs direct the dCas9-FokI fusion proteins to dimerize and cleave both strands of DNA at the target site. In FIG. 2C, the truncated guide RNA approach removes 2-3 nt from the 5' end of the guide RNA but does not modify the Cas9 protein.

DETAILED DESCRIPTION OF THE INVENTION

Figure 1:
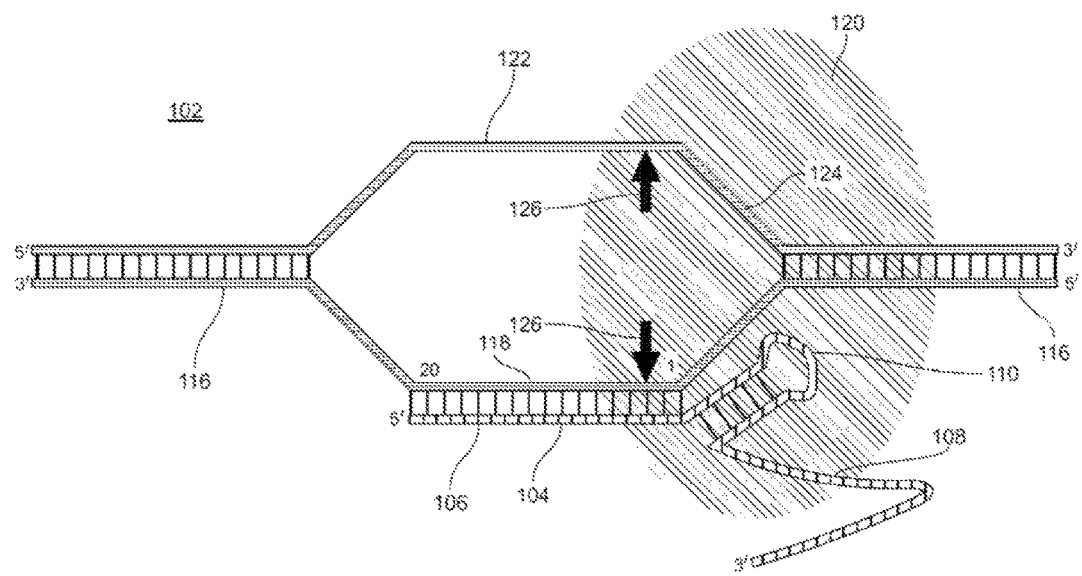
FIG. 1 is a diagram showing an example of CRISPR-Cas9-mediated sequence-specific cleavage of DNA.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

I. Definitions

A nucleic acid refers to a DNA molecule (for example, but not limited to, a cDNA or genomic DNA) or an RNA molecule (for example, but not limited to, an mRNA), and includes DNA or RNA analogs. A DNA or RNA analog can be synthesized from nucleotide analogs. The DNA or RNA molecules may include portions that are not naturally occurring, such as modified bases, modified backbone, deoxyribonucleotides in an RNA, etc. The nucleic acid molecule can be single-stranded or double-stranded.

The term "isolated" when referring to nucleic acid molecules or polypeptides means that the nucleic acid molecule or the polypeptide is substantially free from at least one other component with which it is associated or found together in nature.

As used herein, the term "target nucleic acid" or "target" refers to a nucleic acid containing a target nucleic acid sequence. A target nucleic acid may be single-stranded or double-stranded, and often is double-stranded DNA. A "target nucleic acid sequence," "target sequence" or "target region," as used herein, means a specific sequence or the complement thereof that one wishes to bind to or nick/cleave using a CRISPR system. A target sequence may be within a nucleic acid in vitro or in vivo within the genome of a cell, which may be any form of single-stranded or double-stranded nucleic acid.

A "target nucleic acid strand" refers to a strand of a target nucleic acid that is subject to base-pairing with a guide RNA as disclosed herein. That is, the strand of a target nucleic acid that hybridizes with the crRNA and guide sequence is referred to as the "target nucleic acid strand." The other strand of the target nucleic acid, which is not complementary to the guide sequence, is referred to as the "non-complementary strand." One skilled in the art could appreciate that such a "non-complementary strand" corresponds to the top strand shown in FIG. 1. In the case of double-stranded target nucleic acid (e.g., DNA), each strand can be a "target nucleic acid strand" to design crRNA and guide RNAs and used to practice the methods of this invention as long as there is a suitable PAM site.

An "off-target" nucleic acid refers to a nucleic acid containing sufficient homology with a target nucleic acid so as to be at risk of cleavage by a Cas:gRNA system directed to the target nucleic acid.

"Blocking" refers to preventing, hindering or reducing accessibility of a nucleic acid site from a molecule that would otherwise bind, react with, or target that nucleic acid.

"Hybridization" or "hybridizing" refers to a process where completely or partially complementary nucleic acid strands come together under specified hybridization conditions to form a double-stranded structure or region in which the two constituent strands are joined by hydrogen bonds. Although hydrogen bonds typically form between adenine and thymine or uracil (A and T or U) or cytosine and guanine (C and G), other base pairs may form (e.g., Adams et al., "The Biochemistry of the Nucleic Acids," 11th ed., 1992).

By "cleavage" it is meant the breakage of the covalent backbone of a DNA molecule. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, a complex comprising a guide RNA and a Cas variant is used for targeted single-stranded DNA cleavage, i.e., nicking.

By "nuclease domain" of a nuclease it is meant the polypeptide sequence or domain within the nuclease which possesses the catalytic activity for DNA cleavage. A cleavage domain can be contained in a single polypeptide chain or cleavage activity can result from the association of two (or more) polypeptides. A single nuclease domain may consist of more than one isolated stretch of amino acids within a given polypeptide.

A "Cas9 mutant" or "Cas9 variant" refers to a protein or polypeptide derivative of the wild type *Streptococcus pyogenes* Cas9 protein (i.e., SEQ ID NO: 1), e.g., a protein having one or more point mutations, insertions, deletions, truncations, a fusion protein, or a combination thereof. It retains substantially one or more of the nuclease, RNA binding, or DNA targeting activities of the Cas9 protein. The protein or polypeptide can comprise, consist of, or consist essentially of a fragment of SEQ ID NO: 1. In general, the mutant or variant is at least 50% (e.g., any number between 50% and 100%, inclusive, including but not limited to at least 55%, at least 60%, at least 65%, at least 70%, at least 75%, at least 80%, at least 85%, at least 90%, at least 95%, at least 98%, and at least 99%) identical to SEQ ID NO: 1. The mutant or variant can bind to an RNA molecule and be targeted to a specific DNA sequence via the RNA molecule, and may additionally have a nuclease activity. Examples of these domains include RuvC like motifs (aa. 7-22, 759-766 and 982-989 in SEQ ID NO: 1) and HNH motif (aa 837-863). See Gasiunas et al., Proc Natl Acad Sci USA. 2012 Sep. 25; 109(39): E2579-E2586 and WO2013176772.

A nuclease or a nuclease mutant or variant (e.g., a Cas9 mutant or variant) "having a single-strand nicking activity" refers to a nuclease or a nuclease mutant or variant that has reduced ability to cleave one of two strands of a dsDNA as compared to that to cleave the other strand. For example, the nuclease or a nuclease mutant or variant can have a mutation (e.g., amino acid substitution) that reduces the function of the RuvC domain (or the HNH domain) and as a result reduces the ability to cleave one strand of the target DNA. Examples of such variant include the D10A and H840A Cas9 variants (or variants with another amino acid substitution at position D10 and/or H840), and Cas enzymes for other species with the same substitution at equivalent site.

As used herein, the term "guide RNA" generally refers to an RNA molecule (or a group of RNA molecules collectively) that can bind to a CRISPR protein and target the CRISPR protein to a specific location within a target DNA. A guide RNA can comprise two segments: a DNA-targeting guide segment (which may be referred to as a crRNA segment) and a protein-binding segment (which may be referred to as a tracrRNA segment). The tracrRNA segment has a portion substantially complementary to a portion of the crRNA segment. A "single guide RNA" comprises continuous sequence between and joining the guide segment and the protein binding segment. The DNA-targeting segment comprises a nucleotide sequence that is complementary to (or at least can hybridize to under stringent conditions) a target sequence. The protein-binding segment interacts with a CRISPR protein, such as a Cas9 or Cas9 related polypeptide. These two segments can be located in the same RNA molecule or in two or more separate RNA molecules. When the two segments are in separate RNA molecules, the molecule comprising the DNA-targeting guide segment is sometimes referred to as the guide RNA, while the molecule comprising the protein-binding segment is referred to as the tracrRNA.

The term "orthogonal" means two proteins or nucleic acids which operate independently and do not interfere with each other or with their targets or ligands. For example, a first Cas9 protein and a second Cas9 protein are orthogonal when each forms a complex with a different gRNA, and does not form a complex with the other gRNA.

As used herein, the term "portion" or "fragment" of a sequence refers to any portion of the sequence (e.g., a nucleotide subsequence or an amino acid subsequence) that is smaller than the complete sequence. Portions of polynucleotides can be any length, for example, at least 5, 10, 15, 20, 25, 30, 40, 50, 75, 100, 150, 200, 300 or 500 or more nucleotides in length. A portion of a guide sequence can be about 50%, 40%, 30%, 20%, 10% of the guide sequence, e.g., one-third of the guide sequence or shorter, e.g., 7, 6, 5, 4, 3, or 2 nucleotides in length. The 5' portion of a sequence is located within the 5' one-third of the sequence, the 3' portion is located within the 3' one-third, and the middle portion is within the middle one-third.

As used herein, the term "contacting," when used in reference to any set of components, includes any process whereby the components to be contacted are mixed into same mixture (for example, are added into the same compartment or solution), and does not necessarily require actual physical contact between the recited components. The recited components can be contacted in any order or any combination (or sub-combination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. "Contacting" a target nucleic acid or a cell with one or more reaction components, such as an Cas protein or guide RNA, includes any or all of the following situations: (i) the target or cell is contacted with a first component of a reaction mixture to create a mixture; then other components of the reaction mixture are added in any order or combination to the mixture; and (ii) the reaction mixture is fully formed prior to mixture with the target or cell.

The term "mixture" as used herein, refers to a combination of components, that are interspersed and not in any particular order. Examples of mixtures of elements include a number of different components that are dissolved in the same aqueous solution, or a number of different components attached to a solid support at random or in no particular order in which the different components are not spatially distinct.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention. The term "about" generally refers to plus or minus 10% of the indicated number. For example, "about 10%" may indicate a range of 9% to 11%, and "about 20" may mean from 18-22. Other meanings of "about" may be apparent from the context, such as rounding off, so, for example "about 1" may also mean from 0.5 to 1.4.

II. CRISPR-Cas System

The CRISPR-Cas system is a nucleic acid targeting system originally discovered in prokaryotes that somewhat resemble siRNA/miRNA systems found in eukaryotes. The system consists of an array of short repeats with intervening variable sequences of constant length (i.e., Clusters of regularly interspaced short palindromic repeats, or CRISPRs) and CRISPR-associated (Cas) proteins. In CRISPR, each repetition contains a series of base pairs followed by the same or a similar series in reverse and then by 30 or so base pairs known as "spacer DNA."

The spacers are short segments of DNA from a virus or a plasmid, which have been removed from the virus or plasmid and incorporated into the host genome between the short repeat sequences, and serve as a "memory" of past exposures. The RNA of the transcribed CRISPR arrays is processed by a subset of the Cas proteins into small guide RNAs (which generally have two components as discussed below) containing the viral or plasmid sequences, which direct Cas-mediated cleavage of viral or plasmid nucleic acid sequences that contain so-called protospacer adjacent motif (PAM) site and correspond to the small guide RNAs. The CRISPR-Cas system functions as a prokaryotic immune system, as the spacers recognize and silence exogenous genetic elements in a manner analogous to RNAi in eukaryotic organisms thereby conferring resistance to exogenous genetic elements such as plasmids and phages.

A functional bacterial CRISPR-Cas system requires three components: the Cas protein which provides the nuclease activity and two short, non-coding RNA species referred to as CRISPR RNA (crRNAs) and trans-acting RNA (tracrRNA). The crRNA and tracrRNA together form the above-mentioned guide RNA. Type 1 CRISPR is one of the most well characterized systems and carries out targeted DNA double-strand break in four sequential steps. First, two non-coding RNAs, a pre-crRNA and a tracrRNA, are transcribed from the CRISPR locus. Second, the tracrRNA hybridizes to the repeat regions of the pre-crRNA molecules and mediates processing of pre-crRNA molecules into mature crRNA molecules containing individual spacer sequences. Third, a mature crRNA:tracrRNA complex directs the Cas protein to target DNA via Watson-Crick base-pairing between the spacer on the crRNA and the complement of the protospacer sequence on the target DNA next to a PAM. Finally, the Cas protein catalyzes cleavage of the target DNA to create a double-stranded break within the target site.

Shown in FIG. 1 is a diagram of CRISPR-Cas9-catalyzed sequence-specific cleavage of DNA by a CRISPR-Cas9 system 102. The guide RNA 104 is depicted as an engineered single-guide RNA with a 20-nt guide sequence at the 5' domain 106, which is complementary to a 20-bp target sequence 118 (where 1 and 20 in FIG. 1 represent the beginning and end of the target sequence) in DNA, and a 3' domain 108 (corresponding to the tracrRNA) that binds a Cas9 nuclease 120. The 5' domain 106 has crRNA activity, and the 3' domain 108 has tracrRNA activity. The single-guide RNA comprises a hairpin or duplex structure 110 between the 5' and 3' domains, that is, a continuous sequence between and joining a crRNA segment and a tracrRNA segment. The Cas9:guide RNA complex binds and cleaves a target DNA sequence 116 containing a protospacer 122 directly upstream of a 3-nt PAM site 124. Both strands of the target DNA are cleaved by Cas9 at the sites 126 indicated by arrows.

As discussed above, different strategies have been devised to improve the specificity of CRISPR-Cas9 genome modification.

Figure 2A:
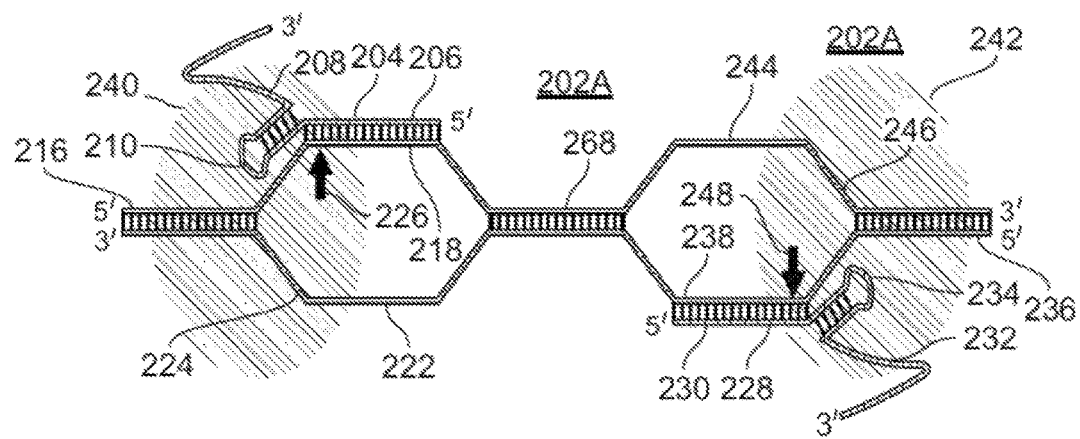
FIGS. 2A-2C are a set of diagrams showing conventional strategies to improve Cas9-mediated cleavage specificity.

FIG. 2A shows a paired nickase strategy using two copies of a Cas9 mutant (Cas9-D10A) 240, 242 in a CRISPR:Cas9-D10A system 202A. The system 202A makes offset single-stranded nicks at two DNA target sites directed by two distinct guide RNA sequences. A first single-guide RNA 204 has a 20-nt guide sequence at the 5' end 206, which is complementary to a 20-bp target nucleic acid sequence 218 in DNA, a 3' domain 208 that binds the first Cas9-D10A 240, and a hairpin or duplex structure 210 between the 5' and 3' domains. The Cas9-D10A:guide RNA complex binds a target DNA 216 containing a protospacer 222 directly upstream of a 3-nt PAM site 224. A first target nucleic acid sequence 218 in the target DNA 216 is cleaved by Cas9-D10A 240 at the cleavage site 226 indicated by arrows but its complementary strand is not cleaved. The system 202A also comprises a second single-guide RNA 228 has a 20-nt guide sequence at the 5' end 230, which is complementary to a second 20-bp target nucleic acid sequence 238 in DNA, a 3' domain 232 that binds the second Cas9-D10A 242, and a hairpin or duplex structure 234 between the 5' and 3' domains. The Cas9-D10A:guide RNA complex binds and cleaves a target DNA 236 containing a protospacer 242 directly upstream of a 3-nt PAM site 244. A second target nucleic acid sequence 238 on a strand opposite the strand having the first target nucleic acid sequence 218 is cleaved by Cas9-D10A 242 at the site 248 indicated by arrows but its complementary strand is not cleaved. By action of the two Cas9-D10A nickases 240, 242, a double stranded break is made in a double stranded DNA.

Figure 2B:
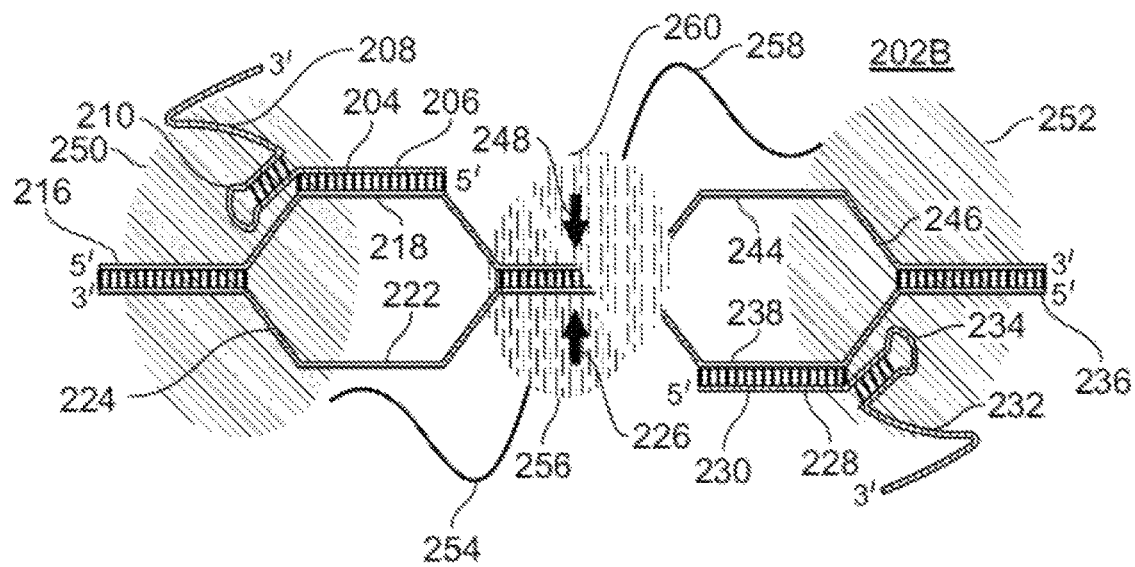

FIG. 2B shows the dimeric RNA-guided FokI nuclease strategy in which catalytically inactive Cas9 proteins (dCas9) 250, 252 are fused to dimerization-dependent FokI nuclease domains 256, 260. The CRISPR:dCas9-FokI system 202B comprises a first single-guide RNA 204 having a 20-nt guide sequence at the 5' end 206, which is complementary to a first target nucleic acid sequence 218 in a first target DNA 216, a 3' domain 208 that binds the first dCas9 250, and a hairpin or duplex structure 210 between the 5' and 3' domains. The first dCas9:guide RNA complex binds a target DNA 216 containing a protospacer 222 directly upstream of a 3-nt PAM site 224. The system 202B also comprises a second single-guide RNA 228 having a 20-nt guide sequence at the 5' end 230, which is complementary to a second target nucleic acid sequence 238, a 3' domain 232 that binds the second dCas9 252, and a hairpin or duplex structure 234 between the 5' and 3' domains. The second dCas9:guide RNA complex binds a target DNA 236 containing a protospacer 242 directly upstream of a 3-nt PAM site 244. A first peptide linker 254 links a first FokI domain 256 to the first dCas9 250, and a second peptide linker 258 links a second FokI domain 260 to the second dCas9 252. The two single-guide RNAs 204, 228 direct the dCas9-FokI fusion proteins to dimerize and cleave both strands of target DNA 216, 236 at the cleavage site 226.

Figure 2C:
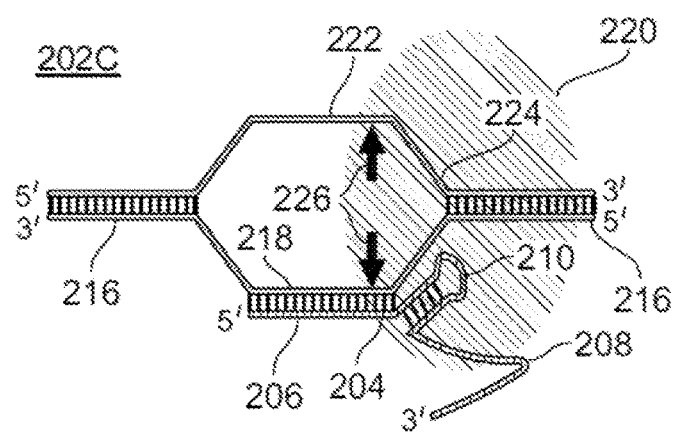

FIG. 2C shows a truncated guide RNA approach which removes 2 or 3 nt from the 5' end of the guide RNA but does not modify the Cas9 protein 220. The CRISPR-Cas9 system 202C has a single-guide RNA 205 has a 17-nt or 18-nt guide sequence at the 5' end 206, which is complementary to a 20-bp target nucleic acid sequence 218 in a target DNA. Use of truncated gRNAs can reduce off-target effects. The truncated single-guide RNA 205 also has a 3' domain 208 that binds the first Cas9-D10A 240, and a hairpin or duplex structure 210 between the 5' and 3' domains. The Cas9:guide RNA complex binds a target DNA 216 containing a protospacer 222 directly upstream of a 3-nt PAM site 224. The target nucleic acid sequence 218 in the target DNA 216 and its complementary strand are cleaved by Cas9 240 to form a double-stranded break at the site 226 indicated by arrows.

Figure 3:
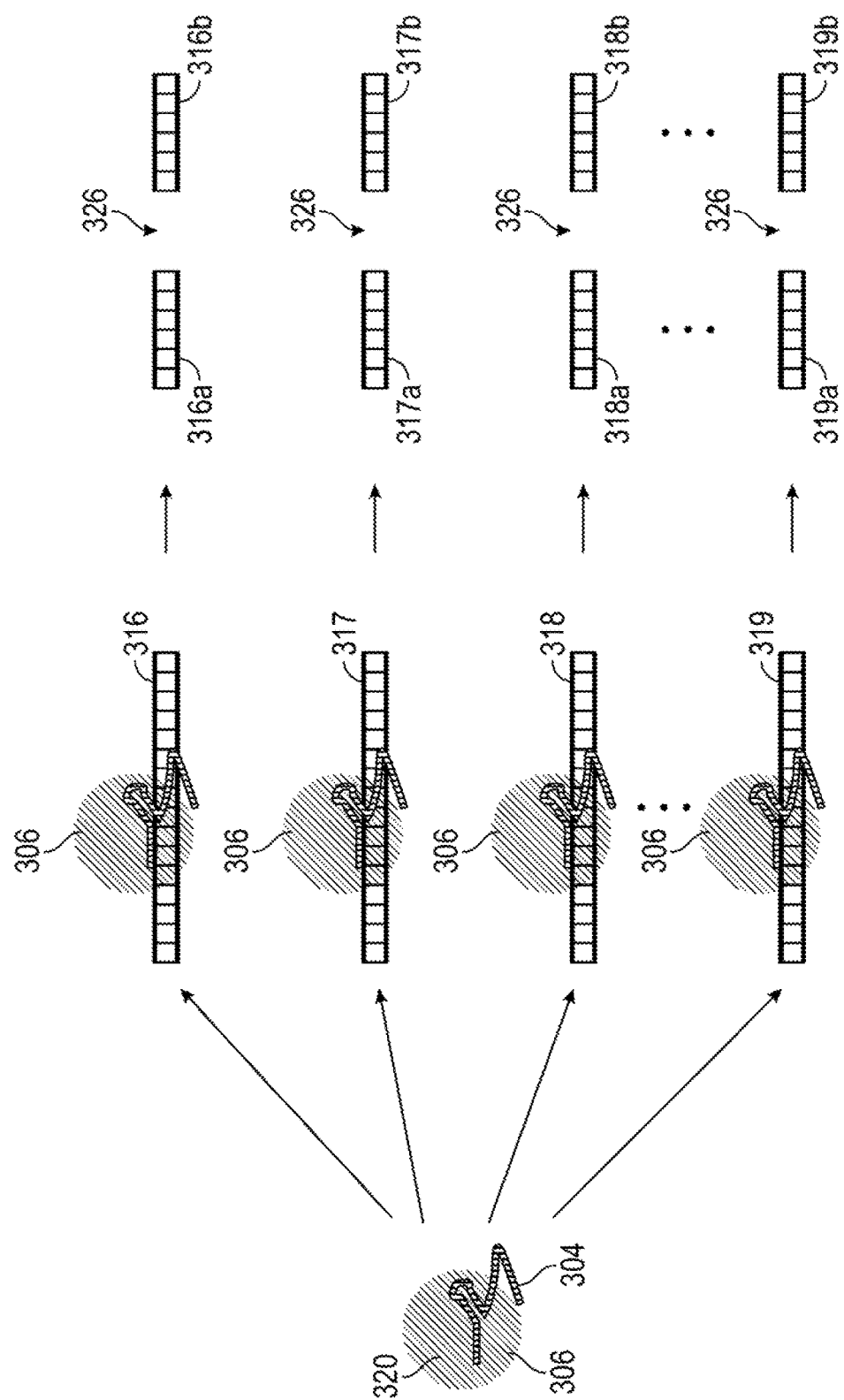
FIG. 3 is a diagram showing standard genome editing with Cas9 RNP that cleaves on-target sites and a panel of off-targets sites.

FIG. 3 is a diagram showing standard genome editing with Cas9 RNP that cleaves on-target sites and a number of off-targets sites. A single guide RNA 304 forms a complex with a Cas9 protein 320. The Cas9:sgRNA complex 306 binds to a target DNA sequence 316 containing a target nucleic acid sequence 318 that is complementary to a guide sequence of the single guide RNA 304. The Cas9:sgRNA complex 306 forms a double-stranded break 326 in the target DNA sequence 316, resulting in first and second segments 316a, 316b. However, the Cas9:sgRNA complex 306 also binds to and cleaves a number of off-target nucleic acid sequence 320, 322, which contain an off-target sequence having sufficient complementarity to the guide sequence of sgRNA 304 for hybridization. A given target DNA, sample, genome or cell may have any number of off-target nucleic acid sequences.

Figure 4:
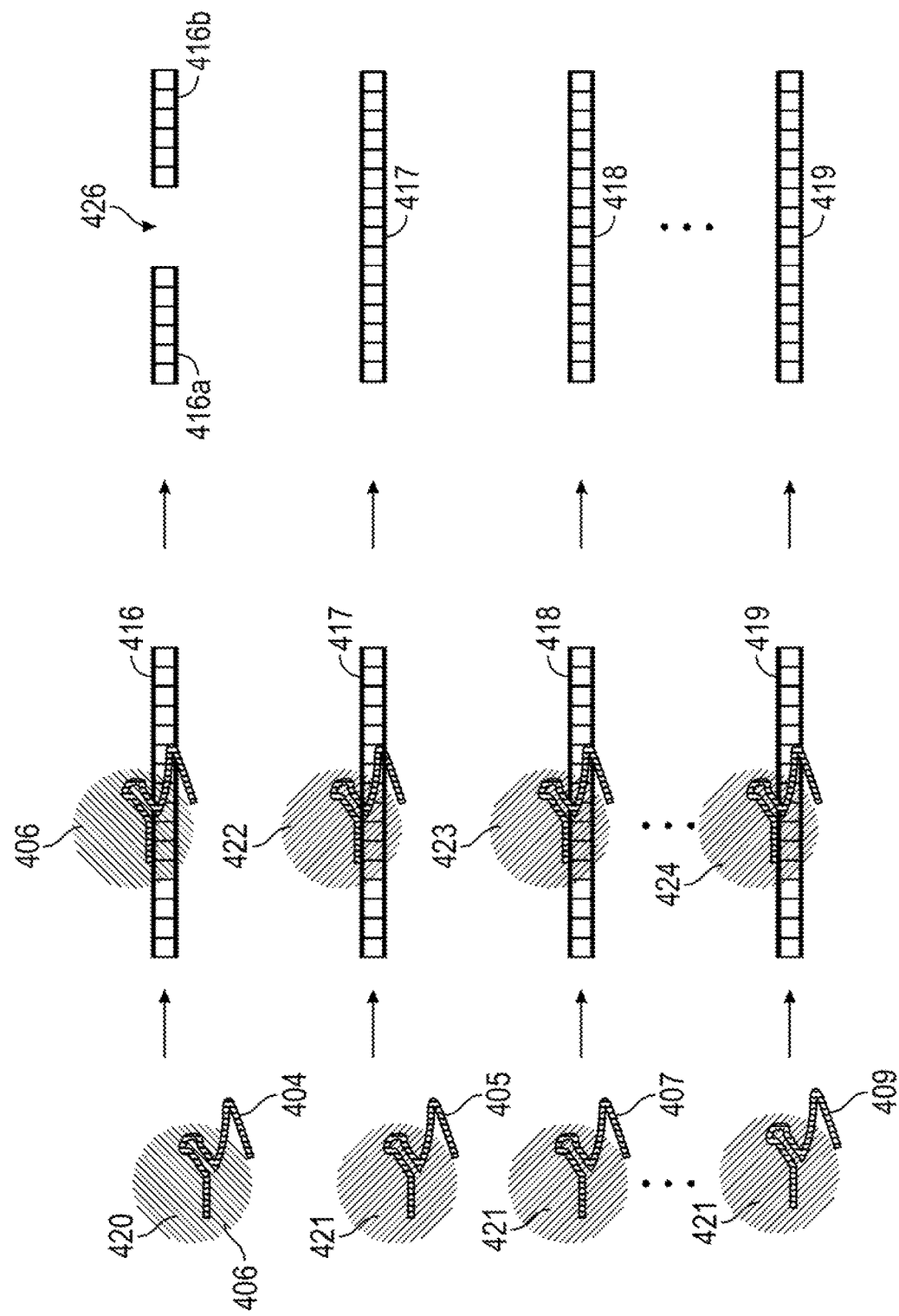
FIG. 4 is a diagram showing an embodiment of the present invention, where Cas:gRNA complexes comprising dCas9 are employed to protect a number of off-target nucleic acid sequences.

FIG. 4 is a diagram showing an embodiment of the present invention, where dCas9 complexes with blocking guide RNAs 405, 407, 409 are employed to protect the off-target sites. More particular, in this embodiment, off-target sequences are identified, and single guide RNAs 405, 407, 409 are prepared so as to have guide sequences complementary to the off-target sequences. Single guide RNAs 405, 407, 409 are complexed with dCas9 421 before being contacted with a sample or genome containing the target DNA sequence 416 and a number of off-target DNA sequences 417, 418, 419. The dCas9:sgRNA complexes 422, 423, 424 bind to the off-target sequences but do not cleave the off-target sequences.

Figure 5:
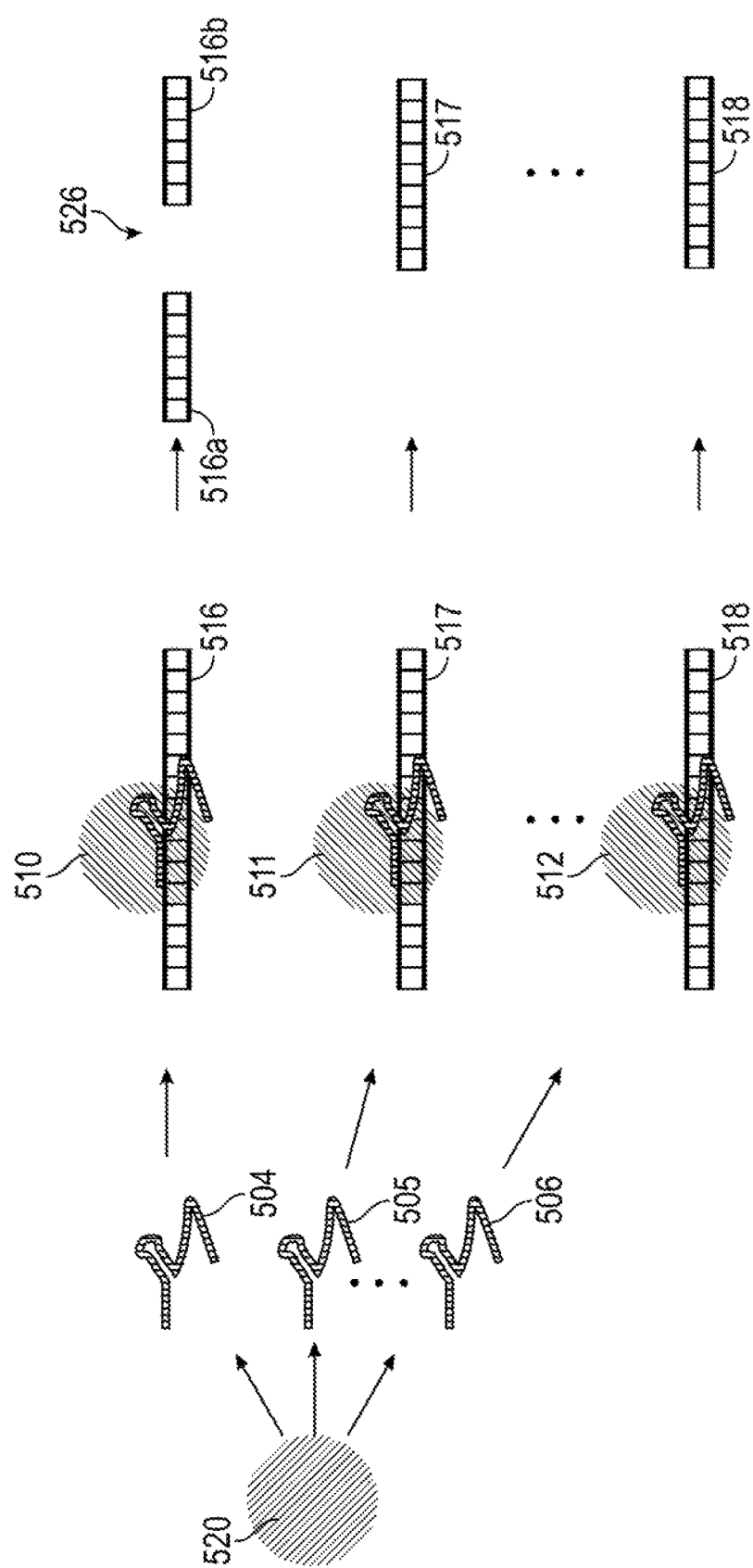
FIG. 5 is a diagram showing an embodiment of the present invention, where Cas:gRNA complexes comprising truncated gRNAs are employed to protect a number of off-target nucleic acid sequences.

FIG. 5 is a diagram showing another embodiment of the present invention, where several Cas9:sgRNA complexes are formed from one active Cas9 protein, and a number of different sgRNAs. One of the complexes is adapted for binding and cleaving a target sequence by virtue of the complex containing an sgRNA (or other guide RNA) comprising 17-25 nt, alternatively 17-20 nt. The other Cas9:sgRNA complexes are adapted for binding at or near off-target sequences, thereby blocking them. FIG. 5 illustrates a truncated guide RNA approach which removes 4-12 nt from the 5' end of a guide RNA so that the truncated gRNA complexes with Cas9 but that complex is not catalytically active, that is, it binds with an off-target nucleic acid sequence but does not cleave or nick it. The guide sequence of the Cas:guide RNA complexes adapted for binding at or near off-target nucleic acid sequences is from 8 to 16 nucleotides in length, alternatively from 10 to 16 nucleotides in length, alternatively from 14 to 16 nucleotides in length, alternatively from 14 to 15 nucleotides in length.

More particularly, FIG. 5 shows a Cas9 protein 520 which is combined with a number of single guide RNAs 504, 505, 506 under conditions favoring the formation of complexes. sgRNA 504 comprises a targeting guide sequence of 20 nt substantially complementary to a target nucleic acid sequence. sgRNA 505 comprises a blocking guide sequence of 16 nt. sgRNA 506 comprises a blocking guide sequence of 14 nt. The blocking guide sequences can be substantially complementary (i) to off-target nucleic acid sequences; (ii) to a portion of the off-target nucleic acid sequences and a nucleic acid adjacent to the portion; or (iii) to a nucleic acid sequences at a location relative to the off-target nucleic acid sequence such that the second Cas:guide RNA complex blocks the first Cas:guide RNA complex from the off-target nucleic acid sequence. sgRNA 504 forms a complex 510 which binds to a target sequence in a target DNA sequence 516 and cleaves the target DNA sequence 516 by forming a double-stranded break, yielding first and second portions 516a, 516b of the target DNA sequence 516. sgRNA 505 forms a complex 511 which binds to a target sequence in an off-target DNA sequence 517 but does not cleaves the target DNA sequence 517, despite the presence of Cas9 because the complex is catalytically inactive due to the presence of a guide RNA of insufficient length. Likewise, sgRNA 506 and 507 form complexes 511, 512 which bind to target sequences in a off-target DNA sequence 518, 519 but does not cleave the off-target DNA sequences 518, 519 due to the presence of a guide RNA of insufficient length to render the complex catalytically active. Thus, off-target DNA sequences 518, 519 remain intact and are not cleaved as a result of blocking them from the catalytically active Cas:sgRNA complex 510.

Figure 6:
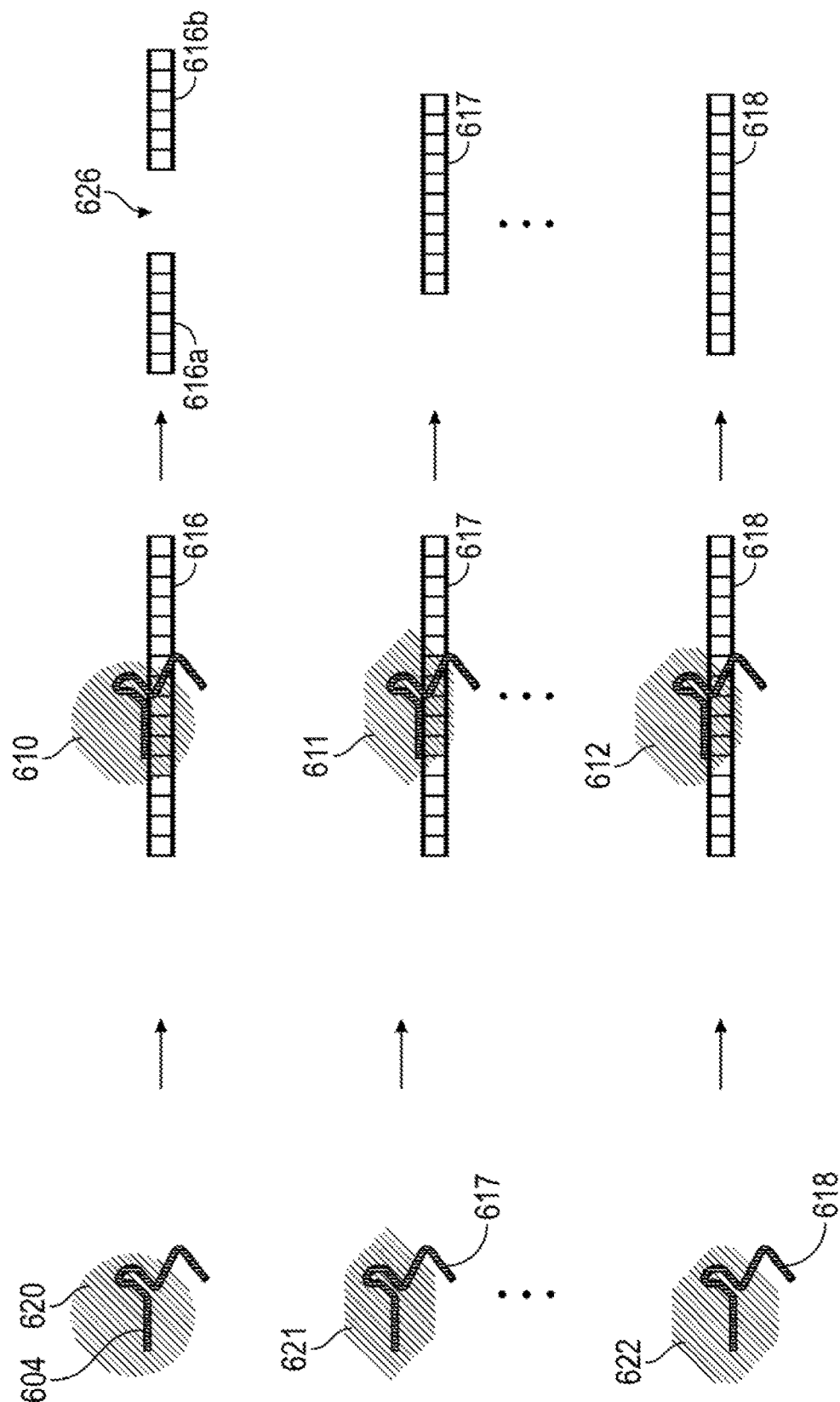
FIG. 6 is a diagram showing an embodiment of the present invention, where different Cas proteins form complexes with different guide RNAs, and gRNAs for off-target nucleic acid sequences form complexes with catalytically inactive Cas protein(s).

FIG. 6 is a diagram showing another embodiment of the present invention, where several Cas:sgRNA complexes are formed from different Cas proteins 620, 621, 622, and a number of different sgRNAs which preferentially complex with different Cas proteins with are catalytically inactive. In some embodiments, the different Cas proteins are orthogonal, in that each Cas protein forms a complex with a different gRNA and does not form a complex with the other gRNA. The Cas proteins can be orthogonal because they form complexes with different tracrRNA sequences. One of the complexes 610 is adapted for binding and cleaving a target sequence in a target DNA 616 by virtue of the complex containing a sgRNA (or other guide RNA) that is substantially complementary to the target sequence. The other Cas proteins are adapted for binding at or near off-target sequences 617, 618, thereby blocking them. FIG. 6 illustrates a multiple Cas protein approach where different Cas proteins 620, 621, 622 bind with different blocking guide sequences to form catalytically inactive complexes, that is, they bind with off-target nucleic acid sequences but do not cleave or nick them. The guide RNAs for the catalytically inactive Cas proteins can have tract RNA segments that form complexes with Cas proteins from species other than the species of the catalytically active Cas9 protein.

For example, the first Cas protein can be Cas9 from *Streptococcus pyogenes*, and the second Cas protein is a dCas protein from an organism other than *Streptococcus pyogenes*, such as *Streptococcus thermophilus*. In this way, the two Cas proteins form complexes with different gRNAs. This facilitates methods and systems where the Cas proteins and gRNAs are separately introduced into a cell or sample containing the target DNA, rather than forming the complex before introduction. It also facilitates introducing a nucleic acid that express the Cas protein.

III. Engineered Guide RNA

Due to its simplicity and efficiency over others, the CRISPR-Cas system has been used to perform genome-editing in cells of various organisms. Yet, as the specificity of this system is dictated by base-pairing between a target DNA and a custom-designed guide RNA, and the system tolerates base-pair mismatching between the target DNA and the guide RNA, undesired off-target DNA binding and cleavage have limited some applications of this system. This invention aims to reduce off-target binding cleavage by a CRISPR-Cas system.

The engineered or synthetic guide RNA of this invention has at least a guide sequence adapted for hybridizing to a DNA sequence of interest.

I. Guide Sequences

Among the components of the systems, methods and compositions disclosed herein, a guide RNA comprising a guide sequence provides the specificity for the DNA which is desired to be bound. It includes a region that is complementary to and capable of hybridization to a pre-selected target site of interest. In various embodiments, this guide sequence can comprise from about 10 nucleotides to more than about 25 nucleotides. For example, the region of base pairing between the guide sequence and the corresponding target site sequence can be about 10, 11, 12, 13, 14, 15, 16, 17, 18, 19, 20, 21, 22, 23, 24, 25, or more than 25 nucleotides in length. In an exemplary embodiment, the guide sequence is about 17-20 nucleotides in length, such as 20 nucleotides.

In the present systems, methods and compositions, a targeting guide sequence may be employed. The targeting guide sequence is a guide sequence that is substantially complementary to and capable of hybridization to a target nucleic acid sequence.

A suitable target nucleic acid has a 3' PAM site/sequence. Each target sequence and its corresponding PAM site/sequence can be selected as a Cas-targeted site. The type 11 CRISPR system, one of the most well characterized systems, employs Cas 9 protein and a guide RNA complementary to a target sequence to affect target cleavage, generally without requiring other system components. The type II CRISPR system of *Streptococcus pyogenes* uses target sites having N12-20NGG, where NGG represent the PAM site from *Streptococcus pyogenes*, and N12-20 represents the 12-20 nucleotides directly 5' to the PAM site. Additional PAM site sequences from other species of bacteria include NGGNG, NNNNGATT, NNAGAA, NNAGAAW, and NAAAAC, where N is any nucleotide (standard or modified) and W is a nucleotide with weak interactions, such as A or T/U. See, e.g., US 20140273233, WO 2013176772, Cong et al., (2012), Science 339 (6121): 819-823, Jinek et al., (2012), Science 337 (6096): 816-821, Mali et al, (2013), Science 339 (6121): 823-826, Gasiunas et al., (2012), Proc Natl Acad Sci USA. 109 (39): E2579-E2586, Cho et al., (2013) Nature Biotechnology 31, 230-232, Hou et al., Proc Natl Acad Sci USA. 2013 Sep. 24, 110(39):15644-9, Mojica et al., Microbiology. 2009 March; 155(Pt 3):733-40, and world wide web address: addgene.org/CRISPR/.

The target nucleic acid strand can be either of the two stands of a target DNA, such as a strand on a genomic DNA in a host cell. Examples of such genomic dsDNA include, but are not necessarily limited to, a host cell chromosome, mitochondrial DNA and a stably maintained plasmid. However, it is to be understood that the present method can be practiced on other dsDNA present in a host cell, such as non-stable plasmid DNA, viral DNA, and phagemid DNA, as long as there is a Cas-targeted site, regardless of the nature of the host cell dsDNA.

2. Blocking Guide Sequence

Another component of the systems, methods and compositions disclosed herein is a blocking guide RNA comprising a blocking guide sequence for an off-target sequence, which is complementary and capable of hybridization to at least a portion of the off-target sequence, or to a sequence sufficiently close to the off-target sequence that the Cas: blocking sequence complex sterically blocks the off-target sequence. The blocking guide sequence can be 5-20 nucleotides long, e.g., 5, 6, 7, 8, 9, 10, 11, 12, 13, 14, 15, 16, 17, 18, 19, or 20 nucleotides in length. In certain embodiments, the blocking guide sequence has at least 90%, alternatively at least 80%, alternatively at least 70% alternatively at least 60%, alternatively at least 50% homology, to the targeting guide sequence.

In certain embodiments, the blocking guide sequence can be substantially complementary to a nucleic acid sequence comprising a portion of an off-target nucleic acid sequence and a flanking nucleic acid sequence adjacent to the portion of the off-target nucleic acid sequence. For example, in certain embodiments, the blocking guide sequence is adapted to hybridize to a nucleic acid sequence comprising a portion of the off-target nucleic acid sequence containing 1 to 10 consecutive nucleotides and a flanking sequence adjacent to the portion of the off-target nucleic acid sequence, the flanking sequence containing 10-19 consecutive nucleotides. Alternatively, in certain embodiments, the blocking guide sequence can be substantially complementary to a nucleic acid sequence at a location relative to the off-target nucleic acid sequence such that the second Cas: guide RNA complex blocks the first Cas:guide RNA complex from the off-target nucleic acid sequence. The blocking guide sequence can bind to a portion of the off-target DNA so as to blocking binding of a catalytically active Cas:gRNA complex, or to blocking unwinding of the off-target nucleic acid sequence. For example, the blocking guide sequence can be substantially complementary to a nucleic acid sequence at a location relative to the off-target nucleic acid sequence such that the second Cas:guide RNA complex sterically hinders the first Cas:guide RNA complex from cleaving the off-target nucleic acid sequence.

To these ends, computational analysis of the whole genome comprising the target nucleic acid sequence and one or more off-target nucleic acid sequences can be performed to identify those off-target nucleic acid sequences and then design and synthesize blocking guide sequences complementary to those off-target nucleic acid sequences.

Also, GC content in the blocking sequence can be used to achieve the desired level of binding affinity for a shorter blocking sequence. Utilizing standard and/or modified nucleotides, the blocking sequence can be designed to base pair with all or a substantial portion of the off-target sequence, thereby blocking this off-target sequence from binding to a catalytically active Cas:gRNA complex.

Thus, Cas9-guided cleavage of a target sequence occurs with improved specificity when a well-designed blocking sequence is included. The blocking sequence may be 3' or 5' with respect to the off-target sequence.

3. Additional Components

Besides the above-described targeting guide sequence and blocking guide sequence, the guide RNA can include additional active or non-active components. In one example, the guide RNA has a tracrRNA segment. For example, the guide RNA can be a single guide RNA molecule where the a guide sequence is continuous with or fused to a tracrRNA to mimic the natural crRNA:tracrRNA duplex. Shown below is an exemplary sgRNA sequence containing crRNA and tracrRNA segments: 5'-(20 nt guide)-GUUUAAGAGC-UAUGCUGGAAACAGCAUAG-CAAGUUUAAAUAAGGCUAGUCCGUU AUCAACUUGAAAAAGUGGCACCGAGUCGGUGC-UUUUUUU-3' (SEQ ID NO:2) (Chen et al. Cell, 2013 Dec. 19; 155(7):1479-91). Various tracrRNA sequences are known in the art and examples include the following tracrRNAs and active portions thereof. As used herein, an active portion of a tracrRNA retains the ability to form a complex with a Cas protein, such as Cas9 or dCas9. See, e.g., WO2014144592. Methods for generating crRNA-tracrRNA hybrid RNAs are known in the art. See e.g., WO2014099750, US 20140179006, and US 20140273226.

```
                                        (SEQ ID NO: 3)
GGAACCAUUCAAAACAGCAUAGCAAGUUAAAAUAAGGCUAGUCCGUUAUC

AACUUGAAAAAGUGGCACCGAGUCGGUGC;

(SEQ ID NO: 4)
UAGCAAGUUAAAAUAAGGCUAGUCCGUUAUCAACUUGAAAAAGUGGCACC

GAGUCGGUGC;

(SEQ ID NO: 5)
AGCAUAGCAAGUUAAAAUAAGGCUAGUCCGUUAUCAACUUGAAAAAGUGG

CACCGAGUCGGUGC;

(SEQ ID NO: 6)
CAAAACAGCAUAGCAAGUUAAAAUAAGGCUAGUCCGUUAUCAACUUGAAA

AAGUGGCACCGAGUCGGUGC;

(SEQ ID NO: 7)
UAGCAAGUUAAAAUAAGGCUAGUCCGUUAUCAACUUGAAAAAGUG;

(SEQ ID NO: 8)
UAGCAAGUUAAAAUAAGGCUAGUCCGUUAUCA;
and (SEQ ID NO: 9)
UAGCAAGUUAAAAUAAGGCUAGUCCG.
```

In some embodiments, the tracrRNA of a guide RNA comprising a blocking sequence is different from the tracrRNA of a guide RNA comprising the targeting sequence. The tracrRNA may be selected so that it forms a complex with a certain Cas9 or CRISPR protein, such as dCas9 from a different species.

In some embodiments, the tracrRNA activity and the guide sequence are included in two separate RNA molecules, which together form the guide RNA. In this case, the molecule with the tracrRNA activity should be able to interact with (usually by base pairing) the molecule having the guide sequence.

The guide RNA can be made by various methods known in the art including cell-based expression, in vitro transcription, and chemical synthesis. The ability to chemically synthesize relatively long RNAs (as long as 200 nucleotides or more) using TC-RNA chemistry (see, e.g., U.S. Pat. No. 8,202,983) allows one to produce guide RNAs with special features that outperform those enabled by the basic four ribonucleotides (A, C, G and U).

Another advantage of chemically synthesizing the blocking sequence is that synthesis allows adjustment of the base-pairing strength of the blocking sequence, specifically by installing one or more modified nucleotides in the blocking sequence to adjust its base-pairing potential. For example, RNA-RNA stems are more stable and have a higher Tm when they have more C and G nucleotides. Accordingly, chemical synthesis of the blocking sequence allows one to install one or more C or G ribonucleotides at select sites in the sequence to strengthen its base pairing with the off-target sequence. In addition, one can incorporate other chemical modifications known to raise or lower the Tm of base pairing. Chemical modifications known to stabilize base pairing include the following: 2'-O-methyl, 2'-fluoro, 2-thiouridine, 4-thiouridine, 2-aminoadenine, and LNA (locked nucleic acid) substituents. Chemical modifications known to weaken base pairing include phosphorothioate, phosphorodithioate, phosphonoacetate (PACE), boranophosphonate, methylphosphonate, and UNA (unlocked nucleic acid) substituents.

Modified RNA oligonucleotides such as locked nucleic acids (LNAs) have been demonstrated to increase the specificity of RNA-DNA hybridization by locking the modified oligonucleotides in a more favorable (stable) conformation. For example, LNA-modified RNA has a modified ribose sugar comprising an additional covalent linkage between the 2' oxygen and 4' carbon which when incorporated into oligonucleotides can improve overall thermal stability and selectivity. Thus in some embodiments, the guide RNAs disclosed herein may comprise one or more modified RNA oligonucleotides. For example, the guide RNA can have chemical modifications in one, some or all of the nucleotides in the guide region or blocking region. Examples of chemically modified nucleotides for RNA include a locked (2'-O-4'-C methylene bridge) nucleotide, 5-methylcytidine, 2'-O-methyl nucleotide, pseudouridine, or a nucleotide in which the ribose phosphate backbone has been replaced by a polyamide chain (peptide nucleic acid), e.g., a synthetic ribonucleic acid.

Existing CRISPR-Cas systems use guide RNA-DNA heteroduplex formation to guide targeting to genomic sites of interest. However, RNA-DNA heteroduplexes can form a more promiscuous range of structures than their DNA-DNA counterparts. In contrast, DNA-DNA duplexes are more sensitive to mismatches, and therefore a DNA-guided nuclease may not bind as readily to off-target sequences, making them comparatively more specific than RNA-guided nucleases. Thus, the guide RNAs described herein can be hybrids, i.e., wherein one or more deoxyribonucleotides, e.g., a short DNA oligonucleotide, replaces all or part of the guide RNA, e.g., all or part of the guide sequence of a guide RNA. In a system where the guide RNA comprises two RNA molecules, one or both can be synthetic and include one or more modified (e.g., locked) nucleotides or deoxyribonucleotides. A system that incorporates DNA into the guide sequence and/or blocking sequence should more reliably target the intended DNA sequences due to the general intolerance of DNA-DNA mismatching, compared to RNA-DNA duplexes. Methods for making such chimeras are known in the art, See, e.g., Barker et al, BMC Genomics. 2005 Apr. 22; 6:57; and Sugimoto et al, Biochemistry. 2000 Sep. 19; 39(37): 11270-81.

By site-specific incorporation of base pair-strengthening and/or -weakening modifications in the blocking sequence or guide sequence, the thermodynamic stability of a blocked sequence or target sequence can be finely tuned to enhance guide RNA specificity without substantially reducing its on-target activity. Other parts of the guide RNA can be modified as well.

Unlike previous strategies to increase Cas9:guide RNA cleavage specificity, the blocked guide RNA approach described herein minimizes reduction in on-target cleavage activity, yielding better results than most Cas9:guide RNA designs described to date. As mentioned above, blocking off-target sequences does not interfere with the cleavage activity at the target site. Also, the CRISPR-Cas systems for the target sequence is not distracted by blocked off-target sequences, so its efficiency is improved. Finally, in contrast to known strategies that employ paired Cas9 nickases (as shown in FIG. 2A) or dimeric dCas9-FokI nucleases (as shown in FIG. 2B), both of which require two guide RNA sequences targeted to appropriately spaced PAM sites, a blocked guide RNA will function with just one PAM-addressable site, making it applicable to a greater number of loci.

IV. Cas:gRNA Complexes and Related Systems

1. Cas:gRNA Complexes

The present disclosure further provides a Cas:guide RNA complex. This complex generally includes three components: (i) a component for enzymatic cleaving or nicking, or binding of a target double-stranded nucleic acid at a specific sequence, (ii) a targeting component comprising a guide sequence, which directs the complex to the correct target sequence, and (iii) a tracr component that recognizes and binds the first component. The first component can be a CRISPR/Cas protein while the latter two can be provided by the above-discussed guide RNA. These two RNAs can be provided as one hybrid RNA molecule known in the art as a single guide RNA (or "sgRNA"), or as two separate RNA molecules.

A "Cas protein," used interchangeably herein with CRISPR protein or CRISPR-Cas protein, refers to a protein of or derived from a CRISPR-Cas type I, type II, or type III system, which has an RNA-guided DNA-binding and/or nuclease activity. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966. See e.g., WO2014144761 WO2014144592, WO2013176772, US20140273226, and US20140273233, the contents of which are incorporated herein by reference in their entireties.

In one embodiment, the Cas protein is derived from a type II CRISPR-Cas system. In exemplary embodiments, the Cas protein is or is derived from a Cas9 protein. The Cas9 protein or other Cas protein can be from *Streptococcus pyogenes, Streptococcus thermophilus, Streptococcus sp., Nocardiopsis dassonvillei, Streptomyces pristinaespiralis, Streptomyces viridochromogenes, Streplomyces viridochromogenes, Streptosporangium roseum, Streptosporangium roseum, Staphylococcus aureus, Alicyclobacillus acidocaldarius, Bacillus pseudomycoides, Bacillus selenitireducens, Exiguobacterium sibiricum, Lactobacillus delbrueckii, lLactobacillus salivaritLs, Microscilla marina, Burkholderiales bacterium, Polaromonas naphthalenivorans, Polaromonas sp., Crocosphaera watsonii, Cyanothece sp., Microcystis aeruginosa, Synechococcus sp., Acelohalobium arabalicum, Ammonifex degensii, Caldicelulosiruptor becscii, Candidatus Desulforudis, Clostridium borulinum, Clostridium dificile, Finegoldia magna, Natranaerobius ihermophilus, Pelotomaculum thermopropionicum, Acidithiobacillus caldus, Acidithiobacillus ferrooxidans, Allochromatium vinosum, Marinobacter sp., Nitrosococcus halophilus, Nitrosoccu watsoni, Pseudoalteromonas haloplankis, Ktedonobacter racemifer, Methanohalobium evesligatum, Anabaena variabilis, Nodularia spumigena, Nostoc sp. Arhrospimr maxima, Arthrospira platensis, Arthrospira sp., Lyngbya sp., Microcoleus chthonoplastes, Oscillatoria sp., Petrotoga mobilis, Thermosipho africanus,* or *Acarvochloris marina.*

In general, a Cas protein includes at least one RNA binding domain. RNA binding domains interact with the guide RNA. The Cas protein can be a wild type CRISPR protein or a modified Cas protein. The Cas protein can be modified to increase nucleic acid binding affinity and/or specificity, alter an enzymatic activity, and/or change another property of the protein. For example, nuclease (i.e., DNase, RNase) domains of the Cas protein can be modified, deleted, or inactivated. Alternatively, the Cas protein can be truncated to remove domains that are not essential for the function of the protein. The Cas protein can also be truncated or modified to optimize the activity of the effector domain.

In some embodiments, the Cas protein can be a mutant of a wild type Cas protein (such as Cas9) or a fragment thereof. Examples of known mutants of Cas9 include the Cas9 nickases such as Cas9-D10A, cleavage-deactivated dCas9, Cas9 mutants with altered PAM specificity such as those disclosed in Kleinstiver et al., "Engineered CRISPR-Cas9 nucleases with altered PAM specificities", Nature 523, 481-485 (2015) (e.g., D1135E SpCas9), and Cas9 mutants from *Staphylococcus aureus* (SaCas9) such as those disclosed in Ran et al., "In vivo genome editing using *Staphylococcus aureus* Cas9", Nature 520, 186-191 (2015). In other embodiments, the CRISPR protein can be derived from a mutant CRISPR protein. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein. In some embodiments, the present system utilizes the Cas9 protein from *Streptococcus pyogenes*, either as encoded in bacteria or as codon-optimized for expression in mammalian cells. Shown below is the amino acid sequence of wild type *S. pyogenes* Cas9 protein sequence (SEQ ID NO: 1, available at world wide web address: uniprot.org/uniprot/Q99ZW2), sometimes referred to as (SpCas9).

(SEQ ID NO: 1)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

-continued

```
YPKLESEFVYGDYKVYDVRKMIAKSEQEIGKATAKYFFYSNIMNFFKTEI

TLANGEIRKRPLIETNGETGEIVWDKGRDFATVRKVLSMPQVNINKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEDLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD
```

The bold letters indicate moieties which have been charged to produce mutants.

A mutant of a wild type Cas protein refers to a polypeptide derivative of the wild type protein, e.g., a protein having one or more point mutations, insertions, deletions, truncations, a fusion protein, or a combination thereof. The mutant has at least one of the RNA-guided DNA binding activity, or RNA-guided nuclease activity, or both. In general, the modified version is at least 50% (e.g., any number between 50% and 100%, inclusive, e.g., 50%, 60%, 70%, 75%, 80%, 85%, 90%, 95%, and 99%) identical to the wild type protein such as SEQ ID NO:1.

A Cas protein described in this invention can be obtained as a recombinant polypeptide. To prepare a recombinant polypeptide, a nucleic acid encoding it can be linked to another nucleic acid encoding a fusion partner, e.g., glutathione-s-transferase (GST), 6x-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide. Alternatively, the polypeptides/proteins can be chemically synthesized (see e.g., Creighton, "Proteins: Structures and Molecular Principles," W.H. Freeman & Co., NY, 1983), or produced by recombinant DNA technology as described herein. For additional guidance, skilled artisans may consult Frederick M. Ausubel et al., Current Protocols in Molecular Biology, John Wiley & Sons, 2003; and Sambrook et al., Molecular Cloning, A Laboratory Manual," Cold Spring Harbor Press, Cold Spring Harbor, N.Y., 2001).

The Cas protein of the present invention can be provided in purified or isolated form, or can be part of a composition. Preferably, where in a composition, the proteins are first purified to some extent, more preferably to a high level of purity (e.g., about 80%, 90%, 95%, or 99% or higher). Compositions according to the invention can be any type of composition desired, but typically are aqueous compositions suitable for use as, or inclusion in, a composition for RNA-guided nuclease reaction. Those of skill in the art are well aware of the various substances that can be included in such nuclease reaction compositions.

Cas protein:guide RNA complexes can be made with recombinant technology using a host cell system or an in vitro translation-transcription system known in the art. Details of such systems and technology can be found in e.g., WO2014144761 WO2014144592, WO2013176772, US20140273226, and US20140273233, the contents of which are incorporated herein by reference in their entireties. The complexes can be isolated or purified, at least to some extent, from cellular material of a cell or an in vitro translation-transcription system in which they are produced.

In any of the embodiments described herein, the Cas protein and the guide RNA may be molecules that do not naturally occur together.

2. Vectors and Host Cells

The present invention also includes vectors and host cells, such as a vector encoding at least two synthetic guide RNAs, wherein a first guide RNA comprises a targeting guide sequence and a second guide RNA comprises a blocking guide sequence, or a host cell transfected with such as vector. The targeting guide sequence, the blocking sequence, the first guide RNA and/or second guide RNA can have any of the features described herein. In certain embodiments, the vector also encodes a Cas protein. In certain embodiments, the vector also encodes at least two Cas proteins, wherein a first of the Cas proteins is adapted to form a complex with the first guide RNA, and a second of the Cas proteins is adapted to form a complex with the second guide RNA, and the first guide RNA comprises a tracrRNA segment that complexes with the first Cas protein and does not complex with the second Cas protein, the second guide RNA comprises a tracrRNA segment that complexes with the second Cas protein and does not complex with the first Cas protein. In certain embodiments, the second Cas protein is a catalytically inactive Cas9 protein, such as dCas9.

To use the guide RNAs and complexes described above, it may be desirable to express them from a nucleic acid that encodes them. This can be performed in a variety of ways. For example, the nucleic acid encoding the guide RNA can be cloned into an intermediate vector for transformation into prokaryotic or eukaryotic cells for replication and/or transcription. Intermediate vectors are typically prokaryotic vectors, e.g., plasmids, or shuttle vectors, or insect vectors, for storage or manipulation of the nucleic acid encoding the guide RNA for production of the guide RNA. The nucleic acid encoding the guide RNA can also be cloned into an expression vector, for administration to a plant cell, animal cell, preferably a mammalian cell or a human cell, fungal cell, bacterial cell, or protozoan cell. Accordingly, the present invention provides a nucleic acid that encodes any of the guide RNAs mentioned above. Preferably, the nucleic acid is isolated and/or purified.

The present invention also provides recombinant constructs or vectors having sequences encoding one or more of the guide RNAs or proteins described above. Examples of the constructs include a vector, such as a plasmid or viral vector, into which a nucleic acid sequence of the invention has been inserted, in a forward or reverse orientation. In a preferred embodiment, the construct further includes regulatory sequences, including a promoter, operably linked to the sequence. Large numbers of suitable vectors and promoters are known to those of skill in the art, and are commercially available. Appropriate cloning and expression vectors for use with prokaryotic and eukaryotic hosts are also described in e.g., Sambrook et al. (2001, Molecular Cloning: A Laboratory Manual, Cold Spring Harbor Press).

A vector refers to a nucleic acid molecule capable of transporting another nucleic acid to which it has been linked. The vector can be capable of autonomous replication or integration into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as inducible regulatory sequences. The design of the expression vector can depend on such factors as the choice of the host cell to be transformed, transfected, or infected, the level of expression of guide RNAs or protein desired, and the like.

Examples of expression vectors include chromosomal, nonchromosomal and synthetic DNA sequences, bacterial plasmids, phage DNA, baculovirus, yeast plasmids, vectors derived from combinations of plasmids and phage DNA, viral DNA such as vaccinia, adenovirus, fowl pox virus, and pseudorabies. However, any other vector may be used as long as it is replicable and viable in the host. The appropriate nucleic acid sequence may be inserted into the vector by a variety of procedures. In general, a nucleic acid sequence encoding one of the RNAs or polypeptides described above can be inserted into an appropriate restriction endonuclease site(s) by procedures known in the art. Such procedures and related sub-cloning procedures are within the scope of those skilled in the art.

The vector may include appropriate sequences for amplifying expression. In addition, the expression vector preferably contains one or more selectable marker genes to provide a phenotypic trait for selection of transformed host cells such as dihydrofolate reductase or neomycin resistance for eukaryotic cell cultures, or such as tetracycline or ampicillin resistance in *E. coli*.

The vectors for expressing the guide RNAs can include RNA Pol III promoters to drive expression of the guide RNAs, e.g., the HI, U6 or 7SK promoters. These human promoters allow for expression of guide RNAs in mammalian cells following plasmid transfection. Alternatively, a T7 promoter may be used, e.g., for in vitro transcription, and the RNA can be transcribed in vitro and purified. Vectors suitable for the expression of short RNAs, e.g., siRNAs, shRNAs, or other small RNAs, can be used.

The vector containing the appropriate nucleic acid sequences as described above, as well as an appropriate promoter or control sequence, can be employed to transform, transfect, or infect an appropriate host to permit the host to express the RNAs or polypeptides described above. Examples of suitable expression hosts include bacterial cells (e.g., *E. coli, Streptomyces, Salmonella typhimurium*), fungal cells (yeast), insect cells (e.g., *Drosophila* and *Spodoptera frugiperda* (Sf9)), animal cells (e.g., CHO, COS, and HEK 293), adenoviruses, and plant cells. The selection of an appropriate host is within the scope of those skilled in the art. In some embodiments, the present invention provides methods for producing the above mentioned RNAs or polypeptides by transforming, transfecting, or infecting a host cell with an expression vector having a nucleotide sequence that encodes one of the RNAs or polypeptides. The host cells are then cultured under a suitable condition, which allows for the expression of the RNAs or polypeptides.

Any of the procedures known in the art for introducing foreign nucleotide sequences into host cells may be used. Examples include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell.

3. Libraries

The present invention also provides collections and libraries of multiple blocking guide RNAs. The library contains two or more of the synthetic guide RNAs for blocking accessibility of off-target sequences. For example, a collection or library comprising two or more guide RNAs, wherein a first guide RNA comprises a first guide sequence substantially complementary to a target nucleic acid sequence, and a second guide RNA comprises a blocking guide sequence substantially complementary (i) to an off-target nucleic acid sequence; (ii) to a portion of the off-target nucleic acid sequence and a nucleic acid adjacent to the portion; or (iii) to a nucleic acid sequence at a location relative to the off-target nucleic acid sequence such that a complex of the second guide RNA with a Cas protein blocks the off-target nucleic acid sequence. In other embodiments, a library (or composition, set, or collection) may include a second guide RNA that comprises a first blocking guide sequence substantially complementary to a first off-target nucleic acid sequence, optionally a third guide RNA comprising a second blocking sequence adapted to hybridize to a second off-target nucleic acid sequence, optionally further comprising a fourth guide RNA comprising a third blocking sequence adapted to hybridize to a third off-target nucleic acid sequence, optionally further comprising a fifth guide RNA comprising a fourth blocking sequence adapted to hybridize to a fourth off-target nucleic acid sequence, optionally further comprising a sixth guide RNA comprising a fifth blocking sequence adapted to hybridize to a fifth off-target nucleic acid sequence, optionally further comprising a seventh guide RNA comprising a sixth blocking sequence adapted to hybridize to a sixth off-target nucleic acid sequence. Also provided is a library containing multiple nucleic acids encoding the RNAs or RNA sets. For example, such a library can contain a library of recombinant expression vectors comprising nucleotides encoding the RNAs or RNA sets. In fact, the collection or library can comprise at least 2, 3, 4, 5, 6, 7, 8, 9, 10 or more blocking guide sequences, wherein each of the blocking guide sequences is substantially complementary to a different off-target nucleic acid sequence. In general, an RNA library can contain from about 10 to about $10^{12}$ individual members, e.g., 10 to about $10^2$, about $10^2$ to about $10^3$, about $10^3$ to about $10^5$, from about $10^5$ to about $10^7$, from about $10^7$ to about $10^9$, or from about $10^9$ to about $10^{12}$ members. An individual member of the library differs from other members of the library in the guide sequence, i.e., the DNA targeting segment of the RNA, or in the blocking sequence. On the other hand, each individual member of a library can contain the same or substantially the same nucleotide sequence of the CRISPR/Cas protein-binding segment as all other members of the library. The library can comprise members that bind to different nucleic acid sequences.

As the synthetic guide RNAs or guide RNA sets disclosed herein reduce off-target sequence cleavage and increase the specificity and on-target activity of the CRISPR-Cas complex, the library allows one to conduct high through-put genomic manipulation and analysis, in which only the DNA-targeting segments of the guide RNAs need to be varied, while the protein-binding segment can be the same. Accordingly, one can carry out a large-scale gene-editing by specifically manipulating or modifying multiple targets at the same time.

4. Kits

This invention further provides kits containing reagents for performing the above-described methods, including CRISPR:Cas guided target binding or nuclease reaction. To that end, one or more of the reaction components, e.g., guide RNAs and Cas proteins, for the methods disclosed herein can be supplied in the form of a kit for use. In one embodiment, the kit comprises a CRISPR protein or a nucleic acid encoding the CRISPR protein, and one or more of a guide RNA described above, a set of RNA molecules described above, and a library described above. In others embodiments, the kit can include one or more other reaction components. In such a kit, an appropriate amount of one or more reaction components is provided in one or more containers or held on a substrate.

Examples of additional components of the kits include, but are not limited to, one or more different polymerases, one or more host cells, one or more reagents for introducing foreign nucleotide sequences into host cells, one or more reagents (e.g., probes or PCR primers) for detecting expression of the RNA or Cas protein or verifying the target nucleic acid's status, and buffers or culture media for the reactions (in 1× or concentrated forms). The kit may also include one or more of the following components: supports, terminating, modifying or digestion reagents, osmolytes, and an apparatus for detection.

The reaction components used can be provided in a variety of forms. For example, the components (e.g., enzymes, RNAs, probes and/or primers) can be suspended in an aqueous solution or as a freeze-dried or lyophilized powder, pellet, or bead. In the latter case, the components, when reconstituted, form a complete mixture of components for use in an assay. The kits of the invention can be provided at any suitable temperature. For example, for storage of kits containing protein components or complexes thereof in a liquid, it is preferred that they are provided and maintained below 0° C., preferably at or below −20° C., or otherwise in a frozen state.

A kit or system may contain, in an amount sufficient for at least one assay, any combination of the components described herein. In some applications, one or more reaction components may be provided in pre-measured single use amounts in individual, typically disposable, tubes or equivalent containers. With such an arrangement, a RNA-guided nuclease reaction can be performed by adding a target nucleic acid, or a sample or cell containing the target nucleic acid, to the individual tubes directly. The amount of a component supplied in the kit can be any appropriate amount and may depend on the target market to which the product is directed. The container(s) in which the components are supplied can be any conventional container that is capable of holding the supplied form, for instance, microfuge tubes, microtiter plates, ampoules, bottles, or integral testing devices, such as fluidic devices, cartridges, lateral flow, or other similar devices.

The kits can also include packaging materials for holding the container or combination of containers. Typical packaging materials for such kits and systems include solid matrices (e.g., glass, plastic, paper, foil, micro-particles and the like) that hold the reaction components or detection probes in any of a variety of configurations (e.g., in a vial, microtiter plate well, microarray, and the like). The kits may further include instructions recorded in a tangible form for use of the components.

V. Uses

As described above, CRISPR/Cas RNA-guided nucleases based on conventional guide RNA can have significant off-target mutagenic effects. Such off-target effects can be problematic for research and for potential therapeutic applications. Therefore, methods for improving the specificity of CRISPR-Cas RNA guided nuclease system and reducing or preventing cleavage of off-target sequences are needed.

The present application provides a method for improving the specificity of CRISPR-Cas guided nuclease system based on a seemingly counterintuitive idea of including a guide RNA designed for an off-target sequence, but making it so that the Cas system with the blocking gRNA binds but does not cleave. As disclosed herein, in one aspect shortening the complementarity region available to base-pair with the off-target binds without cleaving.

Use of blocking guide RNAs substantially reduces off-target effects, yielding improvements of specificity. Thus, the blocking guide RNAs and related methods of this invention provide a highly effective approach for reducing off-target effects without compromising on-target activity. This approach can be implemented on its own or in conjunction with other strategies such as paired nickase method as shown in FIG. 2A to reduce the off-target effects of CRISPR-Cas system.

This method of the invention can be used with Cas proteins other than *S. pyogenes* Cas9, including other Cas proteins from bacteria or archaea as well as Cas9 variants that nick a single strand of DNA or have no nuclease activity, such as the above-mentioned cleavage-deactivated Cas9 bearing catalysis-inactivating mutations in one or both nuclease domains. This method can be applied to systems that utilize a single guide RNA as well as those that use dual RNAs (e.g., the crRNA and tracrRNA activities found in naturally occurring systems).

In one aspect, the present methods, compositions, and systems can be used for modifying a nucleic acid sequence, such as a chromosomal sequence, in a cell, embryo, or animal. The method comprises contacting or introducing into the cell or embryo (a) one or more Cas proteins or nucleic acid encoding the Cas proteins; (b) one or more targeting guide RNAs or DNA encoding the targeting guide RNAs, wherein the targeting guide RNA leads the Cas protein to a target DNA sequence, for example, in the chromosomal sequence, and the Cas:gRNA complex cleaves the chromosomal sequence at the targeted site; (c) either or both of (i) one or more RNA-guided catalytically inactive Cas proteins or nucleic acid encoding such Cas proteins; or (ii) one or more blocking guide RNAs or DNA encoding the blocking guide RNAs. Alternatively, the blocking guide RNA is effective for binding but not cleaving or nicking. The target DNA sequence can contain or be next to a mutation, e.g., point mutation, a translocation or an inversion which may cause or is associated with a disorder. To correct such a mutation, in some embodiments, the method further comprises contacting or introducing into the cell or embryo at least one donor polynucleotide comprising a wild type counterpart of the mutation and at least one sequence having substantial sequence identity with sequence on one side of the targeted site in the chromosomal sequence.

In one aspect, the present methods, compositions, and systems can be used for modifying one or more target nucleic acid sequences in mammalian cells, including but not limited to in primary cells, stem cells, immortalized cells, and conditionally immortalized cells. Among the phenotypes of cells suitable for the present method and guide RNA are chondrocytes, diabetic cells, epithelial cells, fibroblasts, gastrointestinal cells, hematopoietic stem/progenitor and immune cells, hepatocytes, keratinocytes, melanocytes, neural cells, progenitor cells, renal cells, skeletal muscle cells, smooth muscle cells, sertoli cells, and others.

Exemplary Embodiments

Exemplary embodiments provided in accordance with the presently disclosed subject matter include, but are not limited to, the following:

1. A composition comprises at least two synthetic guide RNAs, wherein a first guide RNA comprises a targeting guide sequence and a second guide RNA comprises a blocking guide sequence. The targeting guide sequence is adapted for hybridizing to a target nucleic acid sequence, and the blocking guide sequence is adapted for hybridizing to at least a portion of an off-target nucleic acid sequence.

2. The composition of embodiment 1, wherein the targeting guide sequence is 17-25 nucleotides long. That is, the guide sequence can be 17, 18, 19, 20, 21, 22, 23, 24 or 25 nucleotides long.

3. The composition of any of embodiments 1-2, wherein the targeting guide sequence is 17-20 nucleotides long.

4. The composition of any of embodiments 1-3, wherein the blocking guide sequence is 5-20 nucleotides long. That is, the blocking sequence can be 5, 6, 7, 8, 9, 10, 11, 12, 13, 14, 15, 16, 17, 18, 19, or 20 nucleotides long.

5. The composition of any of embodiments 1-4, wherein the blocking guide sequence is 6-16 nucleotides long, or 7-16 nucleotides long, or 8-16 nucleotides long, or 9-16 nucleotides long, or 10-16 nucleotides long, or 11-16 nucleotides long, or 12-16 nucleotides long, or 13-16 nucleotides long, or 14-16 nucleotides long, or 15-16 nucleotides long.

6. The composition of any of embodiments 1-5, wherein the blocking guide sequence is 9-15 nucleotides long, or 10-15 nucleotides long, or 11-15 nucleotides long, or 12-15 nucleotides long, or 13-15 nucleotides long, or 14-15 nucleotides long.

7. The composition of any of embodiments 1-6, wherein the first guide RNA, the second guide RNA, or both further comprises a tracrRNA sequence.

8. The composition of embodiment 7, wherein the first guide RNA comprises a first tracrRNA sequence, and the second guide RNA comprises a second tracrRNA sequence, and the first and second tracrRNA sequences differ from each other.

9. The composition of embodiment 8, wherein the first guide RNA comprises a first tracrRNA sequence, and the second guide RNA comprises a second tracrRNA sequence, and the first and second tracrRNA sequences differ from each other.

10. The composition of embodiment 9, wherein the first and second tracrRNA sequences are adapted to form complexes with different Cas proteins.

11. The composition of any one of embodiments 1-10, wherein the targeting guide sequence, the blocking guide sequence, or both include one or more modified nucleotides.

12. The composition of any one of embodiments 1-11, further comprising a third guide RNA comprising a second blocking sequence adapted to hybridize to a second off-target nucleic acid sequence, optionally further comprising a fourth guide RNA comprising a third blocking sequence adapted to hybridize to a third off-target nucleic acid sequence, optionally further comprising a fifth guide RNA comprising a fourth blocking sequence adapted to hybridize to a fourth off-target nucleic acid sequence, optionally further comprising a sixth guide RNA comprising a fifth blocking sequence adapted to hybridize to a fifth off-target nucleic acid sequence, optionally further comprising a seventh guide RNA comprising a sixth blocking sequence adapted to hybridize to a sixth off-target nucleic acid sequence.

13. A set, collection or library comprising at least two guide RNAs, wherein a first guide RNA comprises a targeting guide sequence and a second guide RNA comprises a blocking guide sequence. The targeting guide sequence can have any of the features set forth in embodiments 1-3 and 11. The blocking sequence can have any of the features set forth in embodiments 1, 4-6 and 11. The first guide RNA and/or second guide RNA can have any of the features set forth in embodiments 7-10.

14. The set, collection or library of embodiment 13, further comprising a third guide RNA comprising a second blocking sequence adapted to hybridize to a second off-target nucleic acid sequence, optionally further comprising a fourth guide RNA comprising a third blocking sequence adapted to hybridize to a third off-target nucleic acid sequence, optionally further comprising a fifth guide RNA comprising a fourth blocking sequence adapted to hybridize to a fourth off-target nucleic acid sequence, optionally further comprising a sixth guide RNA comprising a fifth blocking sequence adapted to hybridize to a fifth off-target nucleic acid sequence, optionally further comprising a seventh guide RNA comprising a sixth blocking sequence adapted to hybridize to a sixth off-target nucleic acid sequence.

15. A kit comprising a first guide RNA comprises a targeting guide sequence and a second guide RNA comprises a first blocking guide sequence adapted to hybridize to a first off-target nucleic acid sequence. The targeting guide sequence can have any of the features set forth in embodiments 1-3 and 11. The blocking sequence can have any of the features set forth in embodiments 1, 4-6 and 11. The first guide RNA and/or second guide RNA can have any of the features set forth in embodiments 7-10.

16. The kit of embodiment 15, further comprising a third guide RNA comprising a second blocking sequence adapted to hybridize to a second off-target nucleic acid sequence, optionally further comprising a fourth guide RNA comprising a third blocking sequence adapted to hybridize to a third off-target nucleic acid sequence, optionally further comprising a fifth guide RNA comprising a fourth blocking sequence adapted to hybridize to a fourth off-target nucleic acid sequence, optionally further comprising a sixth guide RNA comprising a fifth blocking sequence adapted to hybridize to a fifth off-target nucleic acid sequence, optionally further comprising a seventh guide RNA comprising a sixth blocking sequence adapted to hybridize to a sixth off-target nucleic acid sequence.

17. The kit of any of embodiments 15-16, further comprising at least one Cas protein, or at least one nucleic acid encoding a Cas protein.

18. The kit of embodiment 17, further comprising a second of said at least one Cas protein, or a second of said at least one nucleic acid encoding a Cas protein.

19. The kit of embodiment 18, wherein the second Cas protein is orthogonal to the first Cas protein with respect to guide RNA binding.

20. The kit of any of embodiment 15-19, further comprising a set of instructions for using the guide RNAs.

21. A vector encoding at least two synthetic guide RNAs, wherein a first guide RNA comprises a targeting guide sequence and a second guide RNA comprises a blocking guide sequence. The targeting guide sequence can have any of the features set forth in embodiments 1-3 and 11. The blocking sequence can have any of the features set forth in embodiments 1, 4-6 and 11. The first guide RNA and/or second guide RNA can have any of the features set forth in embodiments 7-10.

22. The vector of embodiment 21, further encoding a Cas protein.

23. The vector of embodiment 22, further encoding at least two Cas proteins, wherein a first of the Cas proteins is adapted to form a complex with the first guide RNA, and a second of the Cas proteins is adapted to form a complex with the second guide RNA, and the first guide RNA comprises a tracrRNA segment that complexes with the first Cas protein and does not complex with the second Cas protein, the second guide RNA comprises a tracrRNA segment that complexes with the second Cas protein and does not complex with the first Cas protein.

24. The vector of embodiment 23, wherein the second Cas protein is a catalytically inactive Cas9 protein, such as dCas9.

25. A method for cleaving a target nucleic acid sequence and blocking an off-target nucleic acid sequence from cleaving with a Cas protein, comprising introducing a vector according to any of embodiments of 21-24 to a cell or sample containing the target DNA; and expressing the vector.

26. A method for cleaving a target nucleic acid sequence and blocking an off-target nucleic acid sequence from cleaving with a Cas protein, comprising:
contacting the target nucleic acid sequence with a first Cas:gRNA complex comprising a Cas protein and a first guide RNA, wherein the first guide RNA comprises a targeting guide sequence substantially complementary to the target nucleic acid sequence, and the first Cas:gRNA complex is catalytically active; and
contacting the off-target nucleic acid sequence with a second Cas:gRNA complex comprising a Cas protein and a second guide RNA, wherein the second guide RNA comprises a blocking guide sequence substantially complementary (i) to an off-target nucleic acid sequence; (ii) to a nucleic acid sequence comprising a portion of the off-target nucleic acid sequence and a flanking nucleic acid sequence adjacent to the portion; or (iii) to a nucleic acid sequence at a location relative to the off-target nucleic acid sequence such that the second Cas:guide RNA complex blocks the first Cas:guide RNA complex from the off-target nucleic acid sequence, wherein the second Cas:guide sequence complex is substantially inactive at cleaving the off-target nucleic acid sequence and blocks the off-target nucleic acid sequence from the first Cas:guide RNA complex. The targeting guide sequence can have any of the features set forth in embodiments 2-3 and 11. The blocking sequence can have any of the features set forth in embodiments 4-6 and 11. The first guide RNA and/or second guide RNA can have any of the features set forth in embodiments 7-10.

27. The method of embodiment 26, wherein the off-target nucleic acid sequence is contacted with a second Cas:gRNA complex before the first Cas:gRNA complex contacts the target nucleic acid sequence.

27. The method of any of embodiments 25-26, further comprising forming the first Cas:guide RNA complex by combining the first guide RNA and at least one of said Cas protein before contacting with the target nucleic acid sequence.

28. The method of any of embodiments 25-27, further comprising forming the second Cas:guide RNA complex by combining the second guide RNA and at least one of said Cas protein before contacting with the off-target nucleic acid sequence.

29. The method of embodiment 28, wherein the second Cas:guide RNA complex comprises a catalytically inactive Cas protein, such as dCas9.

30. The method of embodiment 28, wherein the second Cas:guide RNA complex comprises a catalytically active Cas protein and the second guide RNA is truncated so as to form a catalytically inactive complex.

31. The method of any of embodiments 26-30, further comprising contacting a second off-target nucleic acid sequence with a third Cas:guide RNA complex comprising a second blocking sequence adapted to hybridize to the second off-target nucleic acid sequence, optionally further comprising contacting a third off-target nucleic acid sequence with a fourth Cas:guide RNA complex comprising a third blocking sequence adapted to hybridize to the third off-target nucleic acid sequence, optionally further comprising contacting a fourth off-target nucleic acid sequence with a fifth Cas:guide RNA complex comprising a fourth blocking sequence adapted to hybridize to the fourth off-target nucleic acid sequence, optionally further comprising contacting a fifth off-target nucleic acid sequence with a sixth Cas:guide RNA complex comprising a fifth blocking sequence adapted to hybridize to the fifth off-target nucleic acid sequence, optionally further comprising contacting a sixth off-target nucleic acid sequence with a seventh Cas:guide RNA complex comprising a sixth blocking sequence adapted to hybridize to the sixth off-target nucleic acid sequence.

32. A method for blocking an off-target nucleic acid sequence from cleavage by with a Cas protein, comprising contacting off-target nucleic acid sequence with a blocking Cas:gRNA complex comprising a blocking guide RNA and a Cas protein, wherein the blocking guide RNA comprises a blocking guide sequence substantially complementary (i) to an off-target nucleic acid sequence; (ii) to a nucleic acid sequence comprising a portion of the off-target nucleic acid sequence and a flanking nucleic acid sequence adjacent to the portion; or (iii) to a nucleic acid sequence at a location relative to the off-target nucleic acid sequence such that the Cas:guide RNA complex blocks the off-target nucleic acid sequence from other Cas:guide RNA complexes; and the Cas:guide RNA complex is substantially inactive at cleaving the off-target nucleic acid sequence.

33. The method of any of embodiments 25-32, wherein the target nucleic acid sequence is located in vivo.

34. The method of any of embodiments 25-32, wherein the target nucleic acid sequence is located in vitro.

35. The method of any of embodiments 25-34, wherein the target nucleic acid sequence is located in a cell or embryo, and the method comprises introducing a nucleic acid that expresses the CRISPR protein into the cell or embryo.

36. The method of any of embodiments 25-35, wherein the Cas protein is contacted with the guide RNA or the set of RNA molecules before being contacted with the target nucleic acid sequence.

37. The method of any of embodiments 25-36, wherein the method further comprises purifying or partially purifying a pre-complexed Cas protein and guide RNA before contacting the complex to the target nucleic acid sequence.

38. The method of any embodiment 25, wherein the target nucleic acid sequence is located in a cell or embryo, and the method comprises introducing a vector that expresses the targeting guide RNA and the blocking guide RNA into the cell or embryo.

39. The method of any of embodiments 25-38, wherein the target nucleic acid sequence is a genomic DNA of a microorganism or a cell of a subject.

40. The method of embodiment 39, wherein the target nucleic acid sequence contains a mutation of the subject.

41. The method of embodiment 39, wherein the subject is an animal or a plant.

42. The method of embodiment 41, wherein the animal is a human.

43. The method of embodiment 39, wherein the microorganism is selected from the group consisting of a virus, a bacterium, and a fungus.

44. The method of any of embodiments 25-39, further comprising analyzing a genome comprising the target nucleic acid sequence, and identifying off-target nucleic acid sequences present in the genome.

45. The method of embodiment 44, wherein the analyzing step is performed by whole genome sequencing of a chromosome or cell.

46. The method of embodiment 44 or 45, further comprising designing one or more of the blocking guide sequences based on the identification of the off-target nucleic acid sequences.

47. The method of any of embodiments 25-46, further comprising the step of selecting a second Cas:gRNA complex that either is substantially inactive at cleaving the off-target nucleic acid sequence or blocks the off-target nucleic acid sequence from the first Cas:guide RNA complex, based on the identification of the off-target nucleic acid sequence.

48. The compositions, sets, collection, libraries, kits, vectors, and methods of any of the preceding embodiments, wherein at least one of the Cas proteins is a type 11 CRISPR protein.

49. The compositions, sets, collection, libraries, kits, vectors, and methods of embodiment 48, wherein the type II CRISPR protein is a Cas9 protein.

50. The compositions, sets, collection, libraries, kits, vectors, and methods of embodiment 48, wherein the Cas protein is at least 50% identical to a wild type *S. pyogenes* Cas9 protein (SEQ ID NO:1).

51. The compositions, sets, collection, libraries, kits, vectors, and methods of embodiment 48, wherein the Cas protein comprises the sequence of SEQ ID NO:1.

The foregoing description of exemplary or preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. A composition or kit for gene editing comprising:
at least one Cas protein, or at least one nucleic acid encoding a Cas protein;
a first guide RNA, wherein the first guide RNA and at least one of said Cas protein are adapted to form a first Cas:guide RNA complex, wherein the first guide RNA comprises a targeting guide sequence substantially complementary to a target nucleic acid sequence;
a second guide RNA, wherein the second guide RNA and at least one of said Cas protein are adapted to form a second Cas:guide RNA complex, wherein the second guide RNA comprises a blocking guide sequence substantially complementary (i) to an off-target nucleic acid sequence; (ii) to a nucleic acid sequence comprising a portion of an off-target nucleic acid sequence and a flanking nucleic acid sequence adjacent to the portion; or (iii) to a nucleic acid sequence at a location relative to an off-target nucleic acid sequence such that the second Cas:guide RNA complex blocks the first Cas:guide RNA complex from the off-target nucleic acid sequence;
wherein the second Cas:guide RNA complex is substantially inactive at cleaving the off-target nucleic acid sequence and blocks the off-target nucleic acid sequence from the first Cas:guide RNA complex.

2. The composition or kit of claim 1, wherein the first Cas:guide RNA complex comprises a first Cas protein, and the second Cas:guide RNA complex comprises a second Cas protein, and the second Cas protein is catalytically inactive for cleaving RNA.

3. The composition or kit of claim 2, wherein the second Cas protein is dCas9.

4. The composition or kit of claim 1, wherein the at least one of said Cas protein is a Cas9 protein.

5. The composition or kit of claim 1, wherein the first guide RNA comprises a crRNA segment comprising the targeting guide sequence and a tracrRNA segment having a portion substantially complementary to a portion of the crRNA segment.

6. The composition or kit of claim 5, wherein the crRNA segment and the tracrRNA segment are fused to form a single guide RNA.

7. The composition or kit of claim 1, wherein the first Cas:guide RNA complex comprises a first Cas protein, and the second Cas:guide RNA complex comprises a second Cas protein which is orthogonal to the first Cas protein with respect to guide RNA binding.

8. The composition or kit of claim 7, wherein the first Cas protein is Cas9 from *Streptococcus pyogenes*, and the second Cas protein is Cas9 from an organism other than *Streptococcus pyogenes*.

9. The composition or kit of claim 7, wherein the first guide RNA comprises a tracrRNA segment that complexes with the first Cas protein and does not complex with the second Cas protein, and
the second guide RNA comprises a tracrRNA segment that complexes with the second Cas protein and does not complex with the first Cas protein.

10. The composition or kit of claim 1, wherein the guide sequence of the second Cas:guide RNA complex is from 8 to 16 nucleotides in length.

11. The composition or kit of claim 1, wherein the blocking guide sequence has at least 90% homology to the targeting guide sequence.

12. The composition or kit of claim 1, wherein the blocking guide sequence is adapted to hybridize to a nucleic acid sequence comprising a portion of the off-target nucleic acid sequence containing 1 to 10 consecutive nucleotides and a flanking sequence adjacent to the portion of the off-target nucleic acid sequence, the flanking sequence containing 10-19 consecutive nucleotides.

13. The composition or kit of claim 1, wherein the blocking guide sequence is substantially complementary to a nucleic acid sequence comprising a portion of the off-target nucleic acid sequence containing 1 to 10 consecutive nucleotides and a flanking sequence adjacent to the portion of the off-target nucleic acid sequence, the flanking sequence containing 10-19 consecutive nucleotides.

14. The composition or kit of claim 1, wherein the blocking guide sequence is substantially complementary to a nucleic acid sequence at a location relative to the off-target nucleic acid sequence such that the second Cas:guide RNA complex sterically hinders the first Cas:guide RNA complex from cleaving the off-target nucleic acid sequence.

15. The composition or kit of claim 1, further comprising a third guide RNA, wherein the third guide RNA comprises a second blocking guide sequence substantially complementary (i) to a second off-target nucleic acid sequence; (ii) to a nucleic acid sequence comprising a portion of a second off-target nucleic acid sequence and a flanking nucleic acid adjacent to the portion; or (iii) to a nucleic acid sequence at a location relative to a second off-target nucleic acid sequence such that the third Cas:guide RNA complex blocks the first Cas:guide RNA complex from the second off-target nucleic acid sequence.

16. A collection or library comprising two or more guide RNAs, wherein a first guide RNA comprises a first guide sequence substantially complementary to a target nucleic acid sequence, and a second guide RNA comprises a blocking guide sequence substantially complementary (i) to an off-target nucleic acid sequence; (ii) to a portion of an off-target nucleic acid sequence and a nucleic acid adjacent to the portion; or (iii) to a nucleic acid sequence at a location relative to an off-target nucleic acid sequence such that a complex of the second guide RNA with a Cas protein blocks the off-target nucleic acid sequence.

17. The collection or library of claim 16, wherein the collection or library comprises at least 2 or more blocking guide sequences, wherein each of the blocking guide sequences is substantially complementary to a different off-target nucleic acid sequence.

18. A vector encoding a first guide RNA comprising a first guide sequence substantially complementary to a target nucleic acid sequence, and a second guide RNA comprising a blocking guide sequence substantially complementary (i) to an off-target nucleic acid sequence; (ii) to a portion of an off-target nucleic acid sequence and a nucleic acid adjacent to the portion; or (iii) to a nucleic acid sequence at a location relative to an off-target nucleic acid sequence such that a complex of the second guide RNA with a Cas protein blocks the off-target nucleic acid sequence.

19. The vector of claim 18, further encoding a Cas protein.

20. The vector of claim 19, wherein the Cas protein is inactive for cleaving DNA while retain RNA-guided binding activity.

* * * * *